US007714119B2

(12) United States Patent
Fang et al.

(10) Patent No.: US 7,714,119 B2
(45) Date of Patent: *May 11, 2010

(54) AAV VECTOR COMPOSITIONS AND METHODS FOR ENHANCED EXPRESSION OF IMMUNOGLOBULINS USING THE SAME

(75) Inventors: Jianmin Fang, Palo Alto, CA (US); Karin Jooss, Bellevue, WA (US); Jing Jing Qian, Foster City, CA (US)

(73) Assignee: Biosante Pharmaceuticals, Inc., Lincolnshire, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/179,639

(22) Filed: Jul. 13, 2005

(65) Prior Publication Data

US 2006/0034805 A1    Feb. 16, 2006

Related U.S. Application Data

(60) Provisional application No. 60/587,082, filed on Jul. 13, 2004, provisional application No. 60/659,871, filed on Mar. 10, 2005.

(51) Int. Cl.
*C07H 21/04* (2006.01)
*C12N 15/00* (2006.01)
*C12N 5/00* (2006.01)
*C12N 5/02* (2006.01)
*C12N 15/64* (2006.01)

(52) U.S. Cl. ................. 536/23.53; 435/320.1; 435/325; 435/91.4

(58) Field of Classification Search ....................... None
See application file for complete search history.

(56) References Cited

U.S. PATENT DOCUMENTS

| | | | |
|---|---|---|---|
| 5,310,903 A | 5/1994 | Goulet et al. |
| 5,362,718 A | 11/1994 | Skotnicki et al. |
| 5,436,146 A | 7/1995 | Shenk et al. |
| 5,525,610 A | 6/1996 | Caufield et al. |
| 5,573,500 A | 11/1996 | Katsunuma |
| 5,846,767 A | 12/1998 | Halpin et al. |
| 5,863,765 A | 1/1999 | Berry et al. |
| 6,015,709 A | 1/2000 | Natesan |
| 6,040,183 A | 3/2000 | Ferrari et al. |
| 6,093,570 A | 7/2000 | Ferrari et al. |
| 6,117,680 A | 9/2000 | Natesan et al. |
| 6,133,456 A | 10/2000 | Holt et al. |
| 6,150,527 A | 11/2000 | Holt et al. |
| 6,171,586 B1 | 1/2001 | Lam et al. |
| 6,187,757 B1 | 2/2001 | Clackson et al. |
| 6,261,567 B1 | 7/2001 | Hart et al. |
| 6,306,649 B1 | 10/2001 | Gilman et al. |
| 6,331,415 B1 | 12/2001 | Cabilly et al. |
| 6,479,653 B1 | 11/2002 | Natesan et al. |
| 6,506,379 B1 | 1/2003 | Clackson et al. |
| 6,548,286 B1 | 4/2003 | Samulski et al. |
| 6,602,503 B1 | 8/2003 | Lobb et al. |
| 6,623,940 B1 | 9/2003 | Ledbetter et al. |
| 6,632,800 B1 | 10/2003 | Russell et al. |
| 6,649,595 B2 | 11/2003 | Clackson et al. |
| 6,852,510 B2 | 2/2005 | Bremel et al. |
| 6,911,200 B2 | 6/2005 | Yu et al. |
| 6,933,362 B1 | 8/2005 | Belfort |
| 7,001,596 B1 | 2/2006 | Johnson et al. |
| 7,485,291 B2 | 2/2009 | Fang et al. |
| 7,498,024 B2 | 3/2009 | Fang et al. |
| 2002/0168339 A1 | 11/2002 | Piechaczyk |
| 2002/0168342 A1 | 11/2002 | Wang et al. |
| 2003/0068307 A1 | 4/2003 | Yu |
| 2003/0083290 A1 | 5/2003 | Kingsman et al. |
| 2003/0099616 A1 | 5/2003 | Irving et al. |
| 2003/0099932 A1 | 5/2003 | Lorens et al. |
| 2004/0086485 A1 | 5/2004 | Cordova |
| 2004/0131591 A1 | 7/2004 | Kingsman |
| 2004/0209830 A1 | 10/2004 | Russell |
| 2004/0235011 A1 | 11/2004 | Cooper |

(Continued)

FOREIGN PATENT DOCUMENTS

EP        0623679 A1    11/1994

(Continued)

OTHER PUBLICATIONS

Lu (Stem Cells and Development 13:133-145 (2004)).*
Rudikoff, S., Giusti, A.M., Cook, W.D., and Scharff, M.D. Single amino acid substitution altering antigen-binding specificity. 1982. Proceedings of the National Academy of Sciences, vol. 79, pp. 1979-1983.*
Hamstra, D.A., and Rehemtulla, A. Toward an enzyme/prodrug strategy for cancer gene therapy: edogenous activation of carboxypeptidase A mutants by the PACE/furin family of peptidases. 1999, Human Gene Therapy, vol. 10 pp. 235-248.*
Nakai, H., Herzog, R.W., Hagstrom, J.N., Walter, J., Kung, S., Yang, E.Y., Tai, S.J., Iwaki, Y., Kurtzman, G.J., Fisher, K.J., Colosi, P., Couto, L.B., and High, K.A. Adeno-associated viral vector-mediated gene transfer of human blood coagulation factor IX into mouse liver. 1998, Blood, vol. 91 No. 12, pp. 4600-4607.*

(Continued)

*Primary Examiner*—Larry R. Helms
*Assistant Examiner*—Anne M. Gussow
(74) *Attorney, Agent, or Firm*—Ropes & Gray LLP; James F. Haley, Jr.; Brian M. Gummow

(57) ABSTRACT

Single AAV vector constructs for expression of an immunoglobulin molecule or fragment thereof and methods of making and using the same are described. The AAV vectors comprise a self-processing cleavage sequence between a first and second immunoglobulin coding sequence allowing for expression of a functional antibody molecule using a single promoter. The vector constructs may further include an additional proteolytic cleavage sequence which provides a means to remove the self processing peptide sequence from an expressed immunoglobulin molecule or fragment thereof. The vector constructs find utility in enhanced production of biologically active immunoglobulins or fragments thereof in vitro and in vivo.

17 Claims, 15 Drawing Sheets

U.S. PATENT DOCUMENTS

| | | | |
|---|---|---|---|
| 2004/0235173 | A1 | 11/2004 | Bleck et al. |
| 2004/0265955 | A1* | 12/2004 | Fang et al. ............... 435/69.1 |
| 2005/0003482 | A1* | 1/2005 | Fang et al. ............... 435/69.1 |
| 2005/0042721 | A1* | 2/2005 | Fang et al. ............... 435/69.1 |
| 2005/0095705 | A1 | 5/2005 | Kadan et al. |
| 2006/0034805 | A1 | 2/2006 | Fang et al. |
| 2006/0228336 | A1 | 10/2006 | Ko |
| 2007/0059820 | A1 | 3/2007 | Fang et al. |
| 2007/0065912 | A1 | 3/2007 | Carson et al. |
| 2007/0275915 | A1 | 11/2007 | Hallenbeck et al. |
| 2007/0292922 | A1 | 12/2007 | Fang et al. |
| 2008/0280356 | A1 | 11/2008 | Fang et al. |

FOREIGN PATENT DOCUMENTS

| | | |
|---|---|---|
| ES | 2 172 383 | 9/2002 |
| WO | WO 92/08793 | 5/1992 |
| WO | WO 97/28272 | 8/1997 |
| WO | WO 2004/113493 | 12/2004 |
| WO | WO 2007/126805 | 11/2007 |

OTHER PUBLICATIONS

Green, L.L. Antibody engineering via genetic engineering of the mouse: XenoMouse strains are a vehicle for the-facile generation of therapeutic human monoclonal antibodies. 1999, Journal of Immunological Methods, vol. 231, pp. 11-23.*

Burton et al., Coexpression of factor VIII heavy and light chain adeno-associated viral vectors produces biologically active protein, *Proc. Natl. Acad. Sci, USA*, Oct. 1999, vol. 96, No. 22, pp. 12725-12730.

Hosaka et al., Arg-X-Lys/Arg-Arg Motif as a Signal for Precursor Cleavage Calatyzed by Furin within the Constitutive Secretory Pathway, *J. Biol. Chem.*, Jul. 5, 1991, vol. 266, No. 19, pp. 12127-12130.

Noel et al., High in Vivo Production of a Model Monoclonal Antibody on Adenoviral Gene Transfer, *Human Gene Therapy*, Aug. 2002, vol. 13, pp. 1483-1493.

Pablo de Felipe, et al., "Co-translational, Intraribosomal Cleavage of Polypeptides by the Foot-and-mouth Disease Virus 2A Peptide", The Journal of Biological Chemistry, vol. 278, No. 13, pp. 11441-11448, 2003.

Pablo de Felipe, et al., "Targeting of Proteins Derived from Self-Processing Polyproteins Containing Multiple Signal Sequences", Traffic, vol. 5, pp. 616-626, 2004.

Altschul, et al., "Basic Local Alignment Search Tool", J. Mol. Biol., vol. 215, pp. 403-410, 1990.

Bossis, et al., "Cloning of an Avian Adeno-Associated Virus (AAAV) and Generation of Recombinant AAAV Particles", Jour. of Virology, vol. 77, No. 12, pp. 6799-6810, 2003.

Capecchi, "High Efficiency Transformation by Direct Microinjection of DNA into Cultured Mammalian Cells", Cell, vol. 22, pp. 479-488, 1980.

Chaplin, et al., "Production of Interleukin-12 as a Self-Processing 2A Polypeptide", Jour. of Interferon and Cytokine Res., vol. 19, pp. 235-241, 1999.

Davidson, et al., "Recombinant adeno-associated virus type 2, 4, and 5 vectors: Transduction of variant cell types and regions in the mammalian central nervous system", PNAS, vol. 97, No. 7, pp. 3428-3432, 2000.

de Felipe, et al., "Use of the 2A sequence from foot-and-mouth disease virus in the generation of retroviral vectors for gene therapy", Gene Therapy, vol. 6, pp. 198-208, 1999.

de Felipe, et al., "Tricistronic and Tetracistronic Retroviral Vectors for Gene Transfer", Human Gene Therapy, vol. 11, pp. 1921-1931, 2000.

de Felipe, et al., "Co-translational, Intraribosomal Cleavage of Polypeptides by the Foot-and-mouth Disease Virus 2A Peptide", Jour. of Biol. Chem., vol. 278, No. 13, pp. 11441-11448, 2003.

de Felipe, et al., "Targeting of Proteins Derived from Self-Processing Polyproteins Containing Multiple Signal Sequences", Traffic, vol. 5, pp. 616-626, 2004.

Donnelly, et al., "Analysis of the aphthovirus 2A/2B polyprotein 'cleavage' mechanism indicates not a proteolytic reaction, but a novel translational effect: a putative ribosomal 'skip'", Jour. of Gen. Virology, vol. 82, pp. 1013-1025, 2001.

Donnelly, et al., "The 'cleavage' activities of foot-and-mouth disease virus 2A site-directed mutants and naturally occurring '2A-like' sequences", Jour. of Gen. Virology, vol. 82, pp. 1027-1041, 2001.

Felgner, et al., "Lipofection: A highly efficient, lipid-mediated DNA-transfection procedure", Biochemistry, vol. 84, pp. 7413-7417, 1987.

Furler, et al., "Recombinant AAV vectors containing the foot and mouth disease virus 2A sequence confer efficient bicistronic gene expression in cultured cells and rat substantia nigra neurons", Gene Therapy, vol. 8, pp. 864-873, 2001.

Gao, et al., "Novel adeno-associated viruses from rhesus monkeys as vectors for human gene therapy", PNAS, vol. 99, No. 18, pp. 11854-11859, 2002.

Gao, et al., "Adeno-associated viruses undergo substantial evolution in primates during natural infections", PNAS, vol. 100, No. 10, pp. 6081-6086, 2003.

Green, et al., "Antigen-specific human monoclonal antibodies from mice engineered with human Ig heavy and light chain YACs", Nature Genetics, vol. 7, pp. 13-21, 1994.

Guo, et al., "Evaluation of promoter strength for hepatic gene expression in vivo following adenovirus-mediated gene transfer", Gene Therapy, vol. 3, pp. 802-810, 1996.

Halpin, et al., "Self-processing 2A-polyproteins—a system for co-ordinate expression of multiple proteins in transgenic plants", The Plant Jour., vol. 17, No. 4, pp. 453-459, 1999.

Ill, et al., "Optimization of the human factor VIII complementary DNA expression plasmid for gene therapy of hemophilia A", Blood Coagulation and Fibrinolysis, vol. 8 (suppl 2), pp. 521-530, 1997.

Jackson, et al., "Internal initiation of translation in eukaryotes: The picornavirus paradigm and beyond", RNA, vol. 1, No. 10, pp. 985-1000, 1995.

Jackson, et al., "The Animal Picornavirus", Trends Biochem. Sci., vol. 15, No. 12, pp. 477-483, 1990.

Jakobovits, "Production and selection of antigen-specific fully human monoclonal antibodies from mice engineered with human Ig loci", Advanced Drug Delivery Reviews, vol. 31, pp. 33-42, 1998.

Jakobovits, "Production of fully human antibodies by transgenic mice", Current Opinion in Biotechnology, vol. 6, pp. 561-566, 1995.

Kim, et al., "Use of the human elongation factor 1α promoter as a versatile and efficient expression system", Gene, vol. 91, No. 2, pp. 217-223, 1990.

Klein, et al., "High-velocity microprojectiles for delivering nucleic nucleic acids into living cells", Letters to Nature, vol. 327, pp. 70-73, 1987.

Knott, et al., "Tetracycline-Dependent Gene Regulation: Combinations of Transregulators Yield a Variety of Expression Windows", BioTechniques, vol. 32, No. 4, pp. 796-798, 2002.

Köhler, et al., "Derivation of specific antibody-producing tissue culture and tumor lines by cell fusion", Eur. J. Immunol., vol. 6, pp. 511-519, 1976.

Kotin, "Prospects for the Use of Adeno-Associated Virus as a Vector for Human Gene Therapy", Human Gene Therapy, vol. 5, pp. 793-801, 1994.

Mannino, et al., "Liposome Mediated Gene Transfer", BioTechniques, vol. 6, No. 7, pp. 682-690, 1988.

McCarty, et al., "Self-complementary recombinant adeno-associated virus (scAAV) vectors promote efficient transduction independently of DNA synthesis", Gene, vol. 8, pp. 1248-1254, 2001.

Mendez, et al., "Functional transplant of megabase human immunoglobulin loci recapitulates human antibody response in mice", Nature Genetics, vol. 15, pp. 146-156, 1997.

Mulligan, et al., "Expression of a Bacterial Gene in Mammalian Cells", Science, vol. 209, pp. 1422-1427, 1980.

Needleman, et al., "A General Method Applicable to the Search for Similarities in the Amino Acid Sequence of Two Proteins", J. Mol. Biol., vol. 48, pp. 443-453, 1970.

No, et al., "Ecdysone-inducible gene expression in mammalian cells and transgenic mice", PNAS, vol. 93, pp. 3346-3351, 1996.

Osterwalder, et al., "A conditional tissue-specific transgene expression system using inducible GAL4", PNAS, vol. 98, No. 22, pp. 12596-12601, 2001.

Palmenberg, "Proteolytic Processing of Picornaviral Polyprotein", Annu. Rev. Microbiol., vol. 44, pp. 603-623, 1990.

Passini, et al., "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice", Jour. of Virology, vol. 77, No. 12, pp. 7034-7040, 2003.

Pearson, et al., "Improved tools for biological sequence comparison", PNAS, vol. 85, pp. 2444-2448, 1988.

Rivera, et al., "A humanized system for pharmacologic control of gene expression", Nature Medicine, vol. 2, No. 9, pp. 1028-1032, 1996.

Roosien, et al., "Synthesis of foot-and-mouth disease virus capsid proteins in insect cells using baculovirus expression vectors", Jour. of Gen. Virology, vol. 71, pp. 1703-1711, 1990.

Ryan, et al., "Foot-and-mouth disease virus 2A oligopeptide mediated cleavage of an artificial polyprotein", The EMBO Jour., vol. 13, No. 4, pp. 928-933, 1994.

Ryan, et al., "Cleavage of foot-and-mouth disease virus polyprotein is mediated by residues located within a 19 amino acid sequence", Jour. of Gen. Virology, vol. 72, pp. 2727-2732, 1991.

Ryan, et al., "Specificity of Enzyme-Substrate Interactions in Foot-and-Mouth Disease Virus Polyprotein Processing", Virology, vol. 173, pp. 35-45, 1989.

Shigekawa, et al., "Electroporation of Eukaryotes and Prokaryotes: A General Approach to the Introduction of Macromolecules into Cells", BioTechniques, vol. 6, No. 8, pp. 742-751, 1988.

Smith, "Comparison of Biosequences", Advances in Applied Mathematics, vol. 2, pp. 482-489, 1981.

Southern, et al., "Transformation of Mammalian Cells to Antibiotic Resistance with a Bacterial Gene Under Control of the SV40 Early Region Promoter", Jour. of Molecular and Applied Genetics, vol. 1, pp. 327-341, 1982.

Sugden, et al., "A Vector That Replicates as a Plasmid and Can Be Efficiently Selected in B-Lymphoblasts Transformed by Epstein-Barr Virus", Molecular and Cellular Biology, vol. 5, No. 2, pp. 410-413, 1985.

Suhr, et al., "High level transactivation by a modified *Bombyx* ecdysone receptor in mammalian cells without exogenous retinoid X receptor", PNAS, vol. 95, pp. 7999-8004, 1998.

Szymczak, et al., "Corection of multi-gene deficiency in vivo using a single 'self-cleaving' 2A peptide-based retroviral vector", Nature Biotechnology, vol. 22, No. 5, pp. 589-594, 2004.

Ye, et al., "Regulated Delivery of Therapeutic Proteins After in Vivo Somatic Cell Gene Transfer", Science, vol. 283, pp. 88-91, 1999.

Li et al., A hepatocellular carcinoma-specific adenovirus variant, CV890, eliminates distant human liver tumors in combination with doxorubicin, Cancer Res. 61:6428-6436 (2001).

Burton et al., 1999 "Coexpression of factor VII heavy and light chain adeno-associated viral vectors produces biologically active protein," PNS, 1999 vol. 96: 22: 12725-12730.

Chazenbalk et al., 1996, "Evidence for negative cooperativity among human thyrotropin receptors overexpressed in mammalian cells," Endocrinology 137:4586-4591.

Donnelly, et al. 2001, "Analysis of the Aphthovirus 2A/2B Polyprotein 'Cleavage' Mechanism Indicates Not a Proteolytic Reaction, But a Novel Translational Effect: A Putative Ribosomal 'Skip", J. Virol, 82:1013-1025.

Donnelly, et al., 1997, "The Cleavage Activities of Aphthovirus and Cardiovirus 2A Protein", J. of Virol, 78:13-21.

Furler, et al., 2001, Recombinant AAV Vectors Containing the Foot and Mouth Disease Virus 2A Sequence Confer Efficient Bicistronic Gene Expression in Cultured Cell s and Rat Substantia Nigra Neurons—Gene Therapy 8: 864-873.

Lamikarna et al., 2005, "In vivo evaluation of an EIAV vector for the systemic genetic delivery of therapeutic antibodies," Gene Therapy 12:988-998.

O'Rourke et al., 2002, "Comparison of gene transfer efficiencies and gene expression levels achieved with equine infectious anemia virus- and human immunodeficiency virus type 1-derived lentivirus vectors," J. Virol. 76(3):1510-1515.

Paulas, 1998, "Protein Splicing: A Novel Form of Gene Expression and Paradigm for Self-Catalyzed Protein Rearrangements", Pure & Appl. Chem., 70(1): 1-8.

Xu, 2001, "Optimization of Transcriptional Regulatory Elements for Constructing Plasmid Vecors", Gene 272:149-156.

Collet et al., A binary plasmid system for shuffling combinatorial antibody libraries, Proc. Natl. Acad. Sci. USA 89:10026-10030 (1992).

Loiler et al., Targeting recombinant adeno-associated virus vectors to enhance gene transfer to pancreatic islets and liver, Gene Therapy 10:1551-1558 (2003).

Auricchio et al., "Pharmacological Regulation of Protein Expression from Adeno-Associated Viral Vectors in the Eye," *Mol. Ther.*, 6:238-242 (2002).

Costa et al., "The Cell-Specific Enhancer of the Mouse Transthyretin (Prealbumin) Gene Binds a Common Factor at One Site and a Liver-Specific Factor(s) at Two Other Sites," *Mol. Cell Biol.*, 8:81-90 (1988).

Fang et al., "Stable antibody expression at therapeutic levels using the 2A peptide," *Nature Biotechnology*. 23:584-590 (2005).

Galanis et al., "Phase II Trial of Temsirolimus (CCI-779) in Recurrent Glioblastoma Multiforme: A North Central Cancer Treatment Group Study," *J. Clin. Oncol*,. 23:5294-5304 (2005).

Plate et al., "Vascular Endothelial Growth Factor is a Potential Tumour Angiogenesis Factor in Human Gliomas in Vivo," *Nature*, 359:845-848 (1992).

Rivera et al., "Long-Term Pharmacologically Regulated Expression of Erythropoietin in Primates following AAV-mediated gene transfer," *Blood*, 105:1424-1430 (2005).

Rivera et al., "Long-Term Regulated Expression of Growth Hormone in Mice after Intramuscular Gene Transfer," *PNAS USA*, 96:8657-8662 (1999).

* cited by examiner

SEQUENCE LISTING

<160> NUMBER OF SEQ ID NOS: 27

<210> SEQ ID NO 1

-continued

```
<211> LENGTH: 19
<212> TYPE: PRT
<213> ORGANISM: Foot-and-mouth disease virus

<400> SEQUENCE: 1

Leu Leu Asn Phe Asp Leu Leu Lys Leu Ala Gly Asp Val Glu Ser Asn
 1               5                  10                  15

Pro Gly Pro

<210> SEQ ID NO 2
<211> LENGTH: 19
<212> TYPE: PRT
<213> ORGANISM: Foot-and-mouth disease virus

<400> SEQUENCE: 2

Thr Leu Asn Phe Asp Leu Leu Lys Leu Ala Gly Asp Val Glu Ser Asn
 1               5                  10                  15

Pro Gly Pro

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Leu Lys Leu Ala Gly Asp Val Glu Ser Asn Pro Gly Pro
 1               5                  10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Phe Asp Leu Leu Lys Leu Ala Gly Asp Val Glu Ser Asn Pro Gly
 1               5                  10                  15

Pro

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Leu Leu Asn Phe Asp Leu Leu Lys Leu Ala Gly Asp Val Glu Ser
 1               5                  10                  15

Asn Pro Gly Pro
            20

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Ala Pro Val Lys Gln Thr Leu Asn Phe Asp Leu Leu Lys Leu Ala Gly
  1               5                  10                  15

Asp Val Glu Ser Asn Pro Gly Pro
            20

<210> SEQ ID NO 7
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Thr Glu Leu Leu Tyr Arg Met Lys Arg Ala Glu Thr Tyr Cys Pro
  1               5                  10                  15

Arg Pro Leu Leu Ala Ile His Pro Thr Glu Ala Arg His Lys Gln Lys
            20                  25                  30

Ile Val Ala Pro Val Lys Gln Thr Leu Asn Phe Asp Leu Leu Lys Leu
        35                  40                  45

Ala Gly Asp Val Glu Ser Asn Pro Gly Pro
    50                  55

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Leu Ala Ile His Pro Thr Glu Ala Arg His Lys Gln Lys Ile Val
  1               5                  10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Ala Arg His Lys Gln Lys Ile Val Ala Pro Val Lys Gln Thr Leu
  1               5                  10                  15

Asn Phe Asp Leu Leu Lys Leu Ala Gly Asp Val Glu Ser Asn Pro Gly
            20                  25                  30

Pro

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)
<223> OTHER INFORMATION: Variable amino acid

<400> SEQUENCE: 10

Arg Xaa Lys Arg Arg
 1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ala Lys Arg
 1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Glu Asp Gly Arg
 1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Ala Gly Phe Ala Thr Val Ala Gln Ala
 1               5                  10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Val Pro Arg Gly Ser
 1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Lys Lys Arg
 1
```

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Lys Arg Arg
 1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Arg Arg
 1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Arg Lys Arg
 1

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Arg Lys Lys Arg
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Arg Lys Arg Arg
 1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 21

Lys Arg Arg Lys Arg
 1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ala Lys Arg
 1

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Arg Lys Lys Arg
 1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Arg Lys Arg Arg
 1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Arg Arg Lys Arg
 1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Arg Arg Arg Arg
 1               5

<210> SEQ ID NO 27
<211> LENGTH: 5
```

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid

<400> SEQUENCE: 27

Arg Xaa Arg Lys Arg
 1               5
```

US 7,714,119 B2

AAV VECTOR COMPOSITIONS AND METHODS FOR ENHANCED EXPRESSION OF IMMUNOGLOBULINS USING THE SAME

This application claims priority from U.S. Provisional Application Ser. No. 60/587,082 filed Jul. 13, 2004 and 60/659,871, filed Mar. 10, 2005. The entirety of these provisional applications is incorporated herein by reference.

BACKGROUND OF THE INVENTION

1. Field of the Invention

The invention relates to novel adeno-associated virus (AAV) vector constructs designed to express recombinant full length immunoglobulins or fragments thereof. The AAV vectors may be used for ex vivo or in vivo expression of a heterologous immunoglobulin coding sequence by a cell or organ, or in vitro for the production of recombinant immunoglobulin by AAV transduced cells.

2. Background of the Technology

Monoclonal antibodies have been proven as effective therapeutics for cancer and other diseases. Current antibody therapy often involves repeat administration and long term treatment regimens, which are associated with a number of disadvantages, such as inconsistent serum levels, limited duration of efficacy per administration such that frequent readminstration is required and high cost. The use of antibodies as diagnostic tools and therapeutic modalities has found increasing use in recent years. The first FDA-approved monoclonal antibody for cancer treatment, Rituxan® (Rituximab) was approved in 1997 for the treatment of patients with non-Hodgkin's lymphoma and soon thereafter in 1998, Herceptin®, a humanized monoclonal antibody for treatment of patients with metastatic breast cancer, was approved. Numerous antibody-based therapies that are in various stages of clinical development are showing promise. One limitation to the widespread clinical application of antibody technology is that typically large amounts of antibody are required for therapeutic efficacy and the costs associated with production are significant. Chinese Hamster Ovarian (CHO) cells, SP20 and NSO2 myeloma cells are the most commonly used mammalian cell lines for commercial scale production of glycosylated human proteins such as antibodies. The yields obtained from mammalian cell line production typically range from 50-250 mg/L for 5-7 day culture in a batch fermentor or 300-1000 mg/L in 7-12 days in fed batch fermentors. High level production often relies upon gene amplification and selection of best performing clones which is time consuming and further increases the cost of development and production. In addition, stability issues with respect to antibody-producing cell lines are often evident following multiple passages.

There remains a need for improved systems for the production of full length immunoglobulins and fragments thereof in vitro and in vivo for therapeutic use.

Adeno associated virus (AAV) is a preferred vector for delivering therapeutic genes due to its safety profile and capability of long term gene expression in vivo. Recombinant AAV vectors (rAAV) have been previously used to express single chain antibodies in vivo. Due to the limited transgene packaging capacity of AAV and its low transduction efficiency, it has been a technical challenge to express heavy and light chains of an antibody using a single AAV vector in order to generate full length antibodies.

The present invention addresses this need by demonstrating the feasibility of a novel approach for achieving high and consistent serum levels of full length antibodies following a single injection of a recombinant AAV vector.

SUMMARY OF THE INVENTION

The present invention provides AAV vector compositions and methods for high level expression of full length immunoglobulins or fragments thereof based on expression of immunoglobulin heavy and light chain coding sequences under the transcriptional control of a single promoter.

The invention provides AAV vectors (e.g., AAV6 or AAV8) for expression of recombinant immunoglobulins, wherein the AAV vectors include as operably linked components: a promoter, the partial or complete coding sequence for a first chain of an immunoglobulin molecule, a sequence encoding a self-processing cleavage site and the partial or complete coding sequence for a second chain of an immunoglobulin molecule, wherein the sequence encoding the self-processing cleavage site is located between the coding sequence for the first and second chains of the immunoglobulin molecule. In a related aspect, the invention provides recombinant immunoglobulin molecules and cells generated using the AAV vectors of the invention and methods for making the same.

In one preferred aspect, the self-processing cleavage site comprises a 2A sequence, e.g., a Foot and Mouth Disease Virus (FMDV) sequence. Exemplary 2A peptide sequences are presented as SEQ ID NO:1 and SEQ ID NO:2.

In another preferred aspect, the AAV vector includes an additional proteolytic cleavage site, such as a furin cleavage site with the consensus sequence RXK(R)R (SEQ ID NO:10).

The AAV vectors of the invention may include any of a number of promoters, including, but not limited to an elongation factor 1-alpha promoter (EF1-alpha) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter.

In a further preferred aspect, the heavy and light chain immunoglobulin coding sequences are expressed in an equimolar ratio or close to equimolar ratio.

The invention further provides methods for long term expression of recombinant immunoglobulins in vivo for: treatment of cancer; treatment and prevention of infectious disease; treatment and prevention of autoimmune disease; and for development of preventative vaccines using the AAV described herein, wherein the vector may be administered by any of a number of routes including, but not limited to portal vein (PV) injection, intramuscular (im) injection, intratumoral (it) injection, or intraperitoneal (ip) injection.

BRIEF DESCRIPTION OF THE FIGURES

FIG. 14 discloses SEQ ID NOS: 19-22, respectively, in order of appearance.

FIG. 15 discloses SEQ ID NOS: 23-36, respectively, in order of appearance.

DETAILED DESCRIPTION OF THE INVENTION

Figure 1:
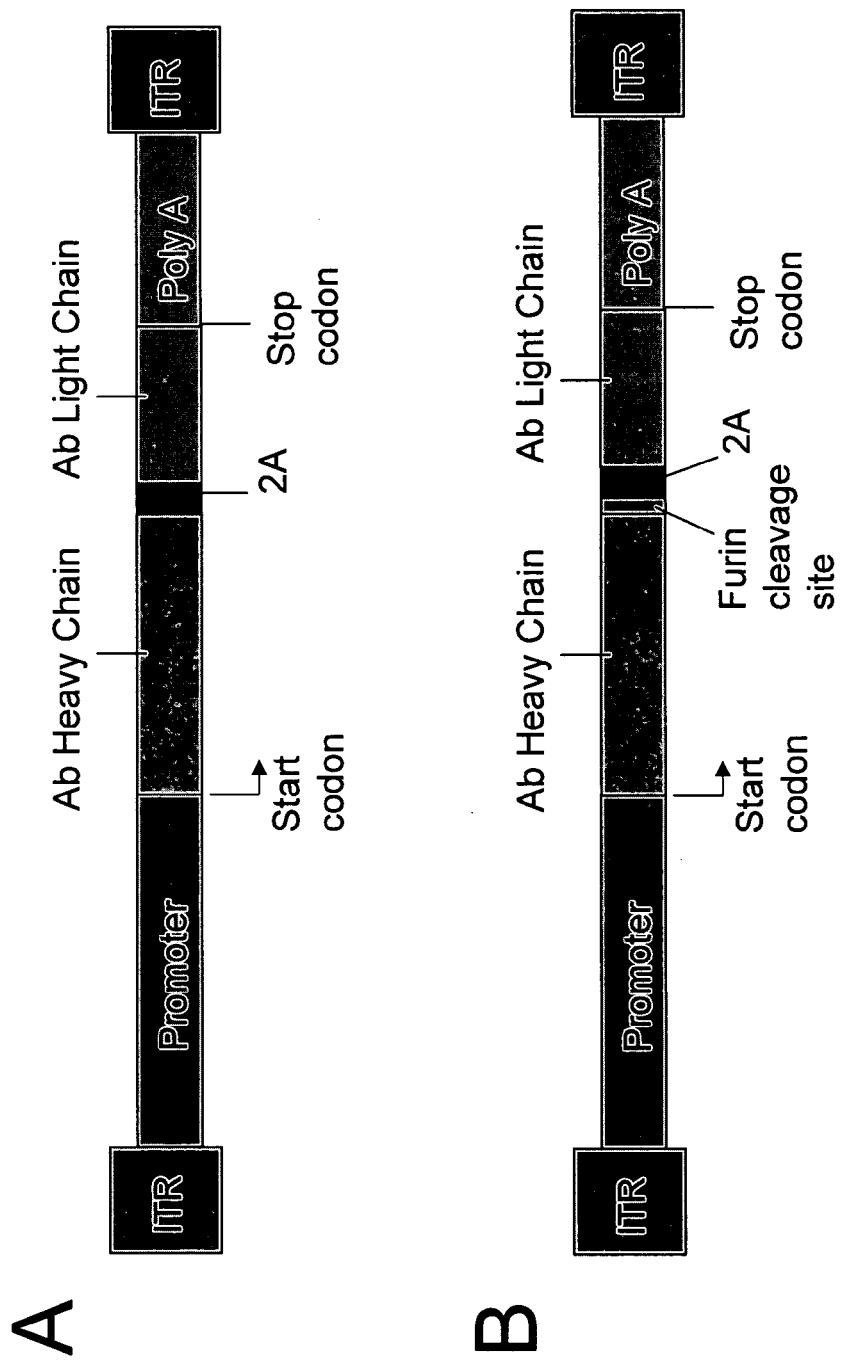
FIGS. 1A and B depict AAV expression cassettes encoding the heavy and light chain for an antibody as described in Example 1, wherein the cassette comprises a 5' AAV ITR, a promoter, the coding sequence for an antibody heavy chain, the coding sequence for a self processing cleavage sequence (exemplified by 2A), the coding sequence for an antibody light chain (H-2A-L), a poly A sequence and a 3' ITR (FIG. 1A). In some embodiments, the vector also includes the coding sequence for an additional proteolytic cleavage site (exemplified by a Furin cleavage site) 5' to the coding sequence for the self processing cleavage sequence (FIG. 1B).

The present invention provides AAV viral vector constructs for expression of recombinant immunoglobulin molecules or fragments thereof and methods for in vitro or in vivo use of the same. The vectors have a self-processing sequence between the heavy and light chain coding sequence of the immunoglobulin allowing for expression of a functional antibody molecule from a single expression cassette driven by a single promoter. Exemplary AAV vector constructs comprise a sequence encoding a self-processing cleavage site between two Ig polypeptide chains and may further comprise an additional proteolytic cleavage site adjacent to the self-processing cleavage site for removal of amino acids derived from the self-processing site remaining following cleavage. The AAV vector constructs of the invention find utility in methods relating to enhanced production of full length biologically active immunoglobulins or fragments thereof in vitro and in vivo.

The various compositions and methods of the invention are described below. Although particular compositions and methods are exemplified herein, it is understood that any of a number of alternative compositions and methods are applicable and suitable for use in practicing the invention. It will also be understood that an evaluation of the AAV immunoglobulin expression constructs and methods of the invention may be carried out using procedures standard in the art.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

DEFINITIONS

Unless otherwise indicated, all terms used herein have the same meaning as they would to one skilled in the art and the practice of the present invention will employ, conventional techniques of microbiology and recombinant DNA technology, which are within the knowledge of those of skill of the art.

The term "vector", as used herein, refers to a DNA or RNA molecule such as a plasmid, virus or other vehicle, which contains one or more heterologous or recombinant DNA sequences and is designed for transfer between different host cells. The terms "AAV expression vector" and "AAV gene therapy vector" refer to any AAV vector that is effective to incorporate and express heterologous DNA sequences in a cell. Any suitable AAV vector can be employed that is effective for introduction of nucleic acids into cells such that protein or polypeptide expression results. Any cells effective for expression, e.g., insect cells and eukaryotic cells such as yeast or mammalian cells are useful in practicing the invention.

The terms "heterologous DNA" and "heterologous RNA" refer to nucleotides that are not endogenous (native) to the cell or part of the genome in which they are present. Generally heterologous DNA or RNA is added to a cell by transduction, infection, transfection, transformation or the like, as further described below. Such nucleotides generally include at least one coding sequence, but the coding sequence need not be expressed. The term "heterologous DNA" may refer to a "heterologous coding sequence" or a "transgene".

As used herein, the terms "protein" and "polypeptide" may be used interchangeably and typically refer to "proteins" and "polypeptides" of interest that are expressed using the self processing cleavage site-containing vectors of the present invention. Such "proteins" and "polypeptides" may be any protein or polypeptide useful for research, diagnostic or therapeutic purposes, as further described below.

The term "replication defective" as used herein relative to a AAV viral vector of the invention means the AAV vector cannot independently replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate further.

The term "operably linked" as used herein relative to a recombinant DNA construct or vector means nucleotide components of the recombinant DNA construct or vector are functionally related to one another for operative control of a selected coding sequence. Generally, "operably linked" DNA sequences are contiguous, and, in the case of a secretory leader, contiguous and in reading frame. However, enhancers do not have to be contiguous.

As used herein, the term "gene" or "coding sequence" means the nucleotide polypeptide in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, "the coding sequence for a first chain of an immunoglobulin molecule or a fragment thereof" refers to a nucleotide sequence encoding a protein molecule including, but not limited to a light chain or heavy chain for an antibody or immunoglobulin, or a fragment thereof.

As used herein, "the coding sequence for a second chain of an immunoglobulin molecule or a fragment thereof" refers to a nucleotide sequence encoding a protein molecule including, but not limited to a light chain or heavy chain for an antibody or immunoglobulin, or a fragment thereof.

A "promoter" is a DNA sequence that directs the binding of RNA polymerase and thereby promotes RNA synthesis, i.e., a minimal sequence sufficient to direct transcription. Promoters and corresponding protein or polypeptide expression may be cell-type specific, tissue-specific, or species specific. Also included in the nucleic acid constructs or vectors of the invention are enhancer sequences which may or may not be contiguous with the promoter sequence. Enhancer sequences influence promoter-dependent gene expression and may be located in the 5' or 3' regions of the native gene.

"Enhancers" are cis-acting elements that stimulate or inhibit transcription of adjacent genes. An enhancer that inhibits transcription also is termed a "silencer". Enhancers can function (i.e., can be associated with a coding sequence) in either orientation, over distances of up to several kilobase pairs (kb) from the coding sequence and from a position downstream of a transcribed region.

A "regulatable promoter" is any promoter whose activity is affected by a cis or trans acting factor (e.g., an inducible promoter, such as an external signal or agent).

A "constitutive promoter" is any promoter that directs RNA production in many or all tissue/cell types at most times, e.g., the human CMV immediate early enhancer/promoter region which promotes constitutive expression of cloned DNA inserts in mammalian cells.

The terms "transcriptional regulatory protein", "transcriptional regulatory factor" and "transcription factor" are used interchangeably herein, and refer to a nuclear protein that binds a DNA response element and thereby transcriptionally regulates the expression of an associated gene or genes. Transcriptional regulatory proteins generally bind directly to a DNA response element, however in some cases binding to DNA may be indirect by way of binding to another protein that in turn binds to, or is bound to a DNA response element.

A "termination signal sequence" within the meaning of the invention may be any genetic element that causes RNA polymerase to terminate transcription, such as for example a polyadenylation signal sequence. A polyadenylation signal sequence is a recognition region necessary for endonuclease cleavage of an RNA transcript that is followed by the polyadenylation consensus sequence AATAAA. A polyadenylation signal sequence provides a "polyA site", i.e. a site on a RNA transcript to which adenine residues will be added by post-transcriptional polyadenylation.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson R J, Howell M T, Kaminski A (1990) Trends Biochem Sci 15(12):477-83) and Jackson R J and Kaminski, A. (1995) RNA 1(10):985-1000. The examples described herein are relevant to the use of any IRES element, which is able to promote direct internal ribosome entry to the initiation codon of a cistron. "Under translational control of an IRES" as used herein means that translation is associated with the IRES and proceeds in a cap-independent manner.

A "self-processing cleavage site" or "self-processing cleavage sequence" is defined herein as a post-translational or co-translational processing cleavage site or sequence. Such a "self-processing cleavage" site or sequence refers to a DNA or amino acid sequence, exemplified herein by a 2A site, sequence or domain or a 2A-like site, sequence or domain. As used herein, a "self-processing peptide" is defined herein as the peptide expression product of the DNA sequence that encodes a self-processing cleavage site or sequence, which upon translation, mediates rapid intramolecular (cis) cleavage of a protein or polypeptide comprising the self-processing cleavage site to yield discrete mature protein or polypeptide products.

As used herein, the term "additional proteolytic cleavage site", refers to a sequence which is incorporated into an expression construct of the invention adjacent a self-processing cleavage site, such as a 2A or 2A like sequence, and provides a means to remove additional amino acids that remain following cleavage by the self processing cleavage sequence. Exemplary "additional proteolytic cleavage sites" are described herein and include, but are not limited to, furin cleavage sites with the consensus sequence RXK(R)R (SEQ ID NO: 10). Such furin cleavage sites can be cleaved by endogenous subtilisin-like proteases, such as furin and other serine proteases within the protein secretion pathway.

As used herein, the terms "immunoglobulin" and "antibody" refer to intact molecules as well as fragments thereof, such as Fa, F(ab')$_2$, and Fv, which are capable of binding an antigenic determinant. Such an "immunoglobulin" and "antibody" is composed of two identical light polypeptide chains of molecular weight approximately 23,000 daltons, and two identical heavy chains of molecular weight 53,000-70,000. The four chains are joined by disulfide bonds in a "Y" configuration. Heavy chains are classified as gamma (IgG), mu(IgM), alpha (IgA), delta (IgD) or epsilon (IgE) and are the basis for the class designations of immunoglobulins, which determines the effector function of a given antibody. Light chains are classified as either kappa or lambda. When reference is made herein to an "immunoglobulin or fragment thereof", it will be understood that such a "fragment thereof" is an immunologically functional immunoglobulin fragment.

The term "humanized antibody" refers to an antibody molecule in which one or more amino acids have been replaced in the non-antigen binding regions in order to more closely resemble a human antibody, while still retaining the original binding activity of the antibody. See, e.g., U.S. Pat. No. 6,602,503.

The term "antigenic determinant", as used herein, refers to that fragment of a molecule (i.e., an epitope) that makes contact with a particular antibody. Numerous regions of a protein or fragment of a protein may induce the production of antibodies which bind specifically to a given region or three-dimensional structure on the protein. These regions or structures are referred to as antigenic determinants. An antigenic determinant may compete with the intact antigen (i.e., the immunogen used to elicit the immune response) for binding to an antibody.

The term "fragment," when referring to a recombinant protein or polypeptide of the invention means a polypeptide which has an amino acid sequence which is the same as part of, but not all of, the amino acid sequence of the corresponding full length protein or polypeptide, which retains at least one of the functions or activities of the corresponding full length protein or polypeptide. The fragment preferably includes at least 20-100 contiguous amino acid residues of the full length protein or polypeptide.

The terms "administering" or "introducing", as used herein refer to delivery of a vector for recombinant protein expression to a cell or to cells and or organs of a subject. Such administering or introducing may take place in vivo, in vitro or ex vivo. A vector for recombinant protein or polypeptide expression may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

"Transformation" is typically used to refer to bacteria comprising heterologous DNA or cells which express an oncogene and have therefore been converted into a continuous growth mode such as tumor cells. A vector used to "transform" a cell may be a plasmid, virus or other vehicle.

Typically, a cell is referred to as "transduced", "infected", "transfected" or "transformed" dependent on the means used for administration, introduction or insertion of heterologous DNA (i.e., the vector) into the cell. The terms "transduced", "transfected" and "transformed" may be used interchangeably herein regardless of the method of introduction of heterologous DNA.

As used herein, the terms "stably transformed", "stably transfected" and "transgenic" refer to cells that have a non-native (heterologous) nucleic acid sequence integrated into the genome. Stable transfection is demonstrated by the establishment of cell lines or clones comprised of a population of daughter cells containing the transfected DNA stably integrated into their genomes. In some cases, "transfection" is not stable, i.e., it is transient. In the case of transient transfection, the exogenous or heterologous DNA is expressed, however, the introduced sequence is not integrated into the genome and is considered to be episomal.

As used herein, "ex vivo administration" refers to a process where primary cells are taken from a subject, a vector is administered to the cells to produce transduced, infected or transfected recombinant cells and the recombinant cells are readministered to the same or a different subject.

A "multicistronic transcript" refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions or polynucleotides are under transcriptional control of a single transcriptional control or regulatory element.

As used herein, a "therapeutic" gene refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

The terms "heterologous" and "exogenous" as used herein with reference to nucleic acid molecules such as promoters and coding sequences, refer to sequences that originate from a source foreign to a particular vector, virus or host cell, or if from the same source, are modified from their original form. Thus, a heterologous gene in a virus or cell includes a gene that is endogenous to the particular virus or cell but has been modified through, for example, codon optimization. The terms also include non-naturally occurring multiple copies of a naturally occurring nucleic acid sequence. Thus, the terms refer to a nucleic acid segment that is foreign or heterologous to the vector, virus or cell, or homologous to the vector, virus or cell but in a position within the vector or cellular genome in which it is not ordinarily found.

The term "homologous" as used herein with reference to nucleotide molecule refers to a nucleic acid sequence naturally associated with a host virus or cell.

The terms "identical" or percent "identity" in the context of two or more nucleotide sequences that are the same or have a specified percentage of amino acid residues or nucleotides that are the same, when compared and aligned for maximum correspondence, as measured using one of the sequence comparison algorithms described herein, e.g. the Smith-Waterman algorithm, or by visual inspection.

As used herein, the term "sequence identity" refers to the degree of identify between nucleotides in two or more aligned sequences, when aligned using a sequence alignment program. The term "% homology" is used interchangeably herein with the term "% identity" herein and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence.

The terms "complement" and "complementary" refer to two antiparallel nucleotide sequences capable of pairing with one another upon formation of hydrogen bonds between the complementary base residues in the antiparallel nucleotide sequences.

The term "native" refers to a gene or protein that is present in the genome of the wildtype virus or cell.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

The term "expression" refers to the transcription and/or translation of an endogenous gene, transgene or coding region in a cell. In the case of an antisense construct, expression may refer to the transcription of the antisense DNA only.

As used herein, the terms "biological activity" and "biologically active", refer to the activity attributed to a particular protein in a cell line in culture or in vivo. The "biological activity" of an "immunoglobulin", "antibody" or fragment thereof refers to the ability to bind an antigenic determinant and thereby facilitate immunological function.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

Immunoglobulins and Fragments Thereof

Antibodies are immunoblobulin proteins that are heterodimers of a heavy and light chain and have proven difficult to express in a full length form from a single vector in mammalian culture expression systems. Three methods are currently used for production of vertebrate antibodies, in vivo immunization of animals to produce "polyclonal" antibodies, in vitro cell culture of B-cell hybridomas to produce monoclonal antibodies (Kohler, et al., Eur. J. Immunol., 6: 511, 1976; Antibodies: A Laboratory Manual, Cold Spring Harbor Laboratory, 1988; incorporated by reference herein) and recombinant DNA technology (described for example in Cabilly et al., U.S. Pat. No. 6,331,415, incorporated by reference herein).

The basic molecular structure of immunoglobulin polypeptides is well known to include two identical light chains with a molecular weight of approximately 23,000 daltons, and two identical heavy chains with a molecular weight 53,000-70,000, where the four chains are joined by disulfide bonds in a "Y" configuration. The amino acid sequence runs from the N-terminal end at the top of the Y to the C-terminal end at the bottom of each chain. At the N-terminal end is a variable region (of approximately 100 amino acids in length) which provides for the specificity of antigen binding.

The present invention is directed to improved methods for production of immunoglobulins of all types, including, but not limited to full length antibodies and antibody fragments having a native sequence (i.e. that sequence produced in response to stimulation by an antigen), single chain antibodies which combine the antigen binding variable region of both the heavy and light chains in a single stably-folded polypeptide chain; univalent antibodies (which comprise a heavy chain/light chain dimer bound to the Fc region of a second heavy chain); "Fab fragments" which include the full "Y" region of the immunoglobulin molecule, i.e., the branches of the "Y", either the light chain or heavy chain alone, or portions, thereof (i.e., aggregates of one heavy and one light chain, commonly known as Fab'); "hybrid immunoglobulins" which have specificity for two or more different antigens (e.g., quadromas or bispecific antibodies as described for example in U.S. Pat. No. 6,623,940); "composite immunoglobulins" wherein the heavy and light chains mimic those from different species or specificities; and "chimeric antibodies" wherein portions of each of the amino acid sequences of the heavy and light chain are derived from more than one species (i.e., the variable region is derived from one source such as a murine antibody, while the constant region is derived from another, such as a human antibody).

The compositions and methods of the invention find utility in production of immunoglobulins or fragments thereof wherein the heavy or light chain is "mammalian", "chimeric" or modified in a manner to enhance its efficacy. Modified antibodies include both amino acid and nucleotide sequence variants which retain the same biological activity of the unmodified form and those which are modified such that the activity is altered, i.e., changes in the constant region that improve complement fixation, interaction with membranes, and other effector functions, or changes in the variable region that improve antigen binding characteristics. The compositions and methods of the invention further include catalytic immunoglobulins or fragments thereof.

A "variant" immunoglobulin-encoding polynucleotide sequence may encode a "variant" immunoglobulin amino acid sequence which is altered by one or more amino acids from the reference polypeptide sequence. The variant polynucleotide sequence may encode a variant amino acid sequence which contains "conservative" substitutions, wherein the substituted amino acid has structural or chemical properties similar to the amino acid which it replaces. In addition, or alternatively, the variant polynucleotide sequence may encode a variant amino acid sequence which contains "non-conservative" substitutions, wherein the substituted amino acid has dissimilar structural or chemical properties to the amino acid which it replaces. Variant immunoglobulin-encoding polynucleotides may also encode variant amino acid sequences which contain amino acid insertions or deletions, or both. Furthermore, a variant "immunoglobulin-encoding polynucleotide may encode the same polypeptide as the reference polynucleotide sequence but, due to the degeneracy of the genetic code, has a polynucleotide sequence which is altered by one or more bases from the reference polynucleotide sequence.

The term "fragment," when referring to a recombinant immunoglobulin of the invention means a polypeptide which has an amino acid sequence which is the same as part of but not all of the amino acid sequence of the corresponding full length immunoglobulin protein, which either retains essentially the same biological function or activity as the corresponding full length protein, or retains at least one of the functions or activities of the corresponding full length protein. The fragment preferably includes at least 20-100 contiguous amino acid residues of the full length immunoglobulin.

The potential of antibodies as therapeutic modalities is currently limited by the production capacity and excessive cost of the current technology. The single rAAV vector immunoblobulin expression system of the invention permits the expression and delivery of two or more coding sequences, i.e., immunoglobulins with bi- or multiple-specificities from a single AAV vector. The present invention addresses the limitations in the prior art and is applicable to any immunoglobulin (i.e. an antibody) or fragment thereof as further detailed herein, including engineered antibodies, e.g., single chain antibodies, full-length antibodies or antibody fragments.

The invention relies on the expression of immunoglobulin heavy and light chains using a single promoter wherein the heavy and light chains are expressed in substantially equal ratios. The linking of proteins in the form of polyproteins is a strategy adopted in the replication of many viruses including picomaviridae. Upon translation, virus-encoded self-processing peptides mediate rapid intramolecular (cis) cleavage of the polyprotein to yield discrete mature protein products. The present invention provides advantages over the use of an IRES in that a vector for recombinant immunoglobulin expression comprising a self-processing peptide (exemplified herein by 2A peptides) is provided which facilitates expression of immunoglobulin heavy and light chain coding sequences using a single promoter, wherein the immunoglobulin heavy and light chain coding sequences are expressed in a substantially equimolar ratio. The expression of heavy and light chains in substantially equal molar ratios may be demonstrated, for example, by Western blot analysis, where the heavy and light chain proteins are separated by SDS-PAGE under reducing conditions, probed using an anti-rat or anti-human IgG polyclonal antibody and visualized using commercially available kits according to the manufacturer's instructions.

Agonistic Anti-VEGFR2 Antibody

The present invention provides AAV compositions and methods for production of essentially any immunoglobin. One example of an immunogloblin with clinical utility that can be produced using the compositions and methods of the invention is an agonistic anti-VEGFR2 antibody.

By way of background, vascular endothelial cell growth factor (VEGF) is a growth factor that plays a crucial role in the development of the vascular system and neovascularization (angiogenesis). VEGF stimulates proliferation, migration, and differentiation of vascular endothelial cells and induces blood vessel formation in both physiological and pathological conditions. VEGF binds to three cell surface tyrosine receptors, VEGFR1, VEGFR2 (KDR) and VEGFR3, in which VEGFR2 is crucial in mediating VEGF activated signal transduction.

In pathological conditions where blood supply is insufficient, such as coronary artery disease, skeletal ischemia, myocardial ischemia, brain ischemia, limb ischemia, peripheral vascular diseases, ischemic skin wounds, etc., angiogenesis and neo-vascularization is often desired to improve local blood circulation. Administration of angiogenic growth factors, particularly VEGF, has been shown in preclinical models to be effective in neo-vascularizing ischemic tissues. VEGF is now under clinical evaluation for cardiac and skeletal ischemia. However, recombinant VEGF has a half-life of approximately 30 minutes in humans. The short half-life of VEGF limits its clinical applications. Therefore, agonistic anti-KDR antibodies providing VEGF function, but having a long half-life will improve angiogenic therapies.

The compositions and methods of the present invention provide a means for high level expression of immunoglobulins, one example of which is an agonistic human anti-VEGFR2 antibody in vivo. The invention finds particular utility in situations where administration of the antibody itself may exhibit a lack of therapeutic efficacy due to short half-life and resulting inconsistent immunoglobulin levels in vivo, in addition to the inconvenience and cost of repeat administration. Although VEGF may be administered as a recombinant protein, expression of an agonistic anti-VEGFR antibody using the AAV vectors of the invention provides the advantage of consistent and high level immunoglobulin expression.

The invention provides an agonistic human anti-VEGFR2 antibody, designated as CGI 2.20. The antibody specifically binds to human VEGFR2, the main receptor for VEGF mediated angiogenesis. CGI 2.20 has been observed to stimulate vascular endothelial cell proliferation in vitro in a dose-dependent manner and can mimic VEGF function. Furthermore, CGI 2.20 was developed in transgenic mice bearing the human IgG gene, designated the XENOMOUSE™ and, therefore, is a completely human antibody that would unlikely cause a host immune response when administered in vivo in human patients. This antibody may be used as a pro-angiogenic agent to induce neovascularization in vascular diseases.

The CGI 2.20 mAb may be administrated locally or systematically by any vector system routinely employed by those of skill in the art (viral or non-viral). Vectors include but are not limited to viral vectors such as AAV, adenovirus, retrovirus, lentivirus etc., and non-viral vectors, such as plasmids.

The CGI 2.20 mAb may be used therapeutically as a means to induce neovascularization for treatment of diseases, including but not limited to, coronary artery disease, skeletal ischemia, myocardial ischemia, brain ischemia, limb ischemia, peripheral vascular diseases, ischemic skin wounds, etc. The recombinant antibody may be a whole antibody or antibody fragments, e.g., a single chain antibody, an Fab, an F(ab)2, or the like. Example 7 describes studies employing the CGI 2.20 mAb.

Self-Processing Cleavage Sites or Sequences

A "self-processing cleavage site" or "self-processing cleavage sequence" as defined above refers to a DNA or amino acid sequence, wherein upon translation, rapid intramolecular (cis) cleavage of a polypeptide comprising the self-processing cleavage site occurs to yield discrete mature protein products. Such a "self-processing cleavage site", may also be referred to as a post-translational or co-translational processing cleavage site, exemplified herein by a 2A site, sequence or domain. A 2A site, sequence or domain demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly, 2001). Alternatively, a 2A site or domain demonstrates "auto-proteolysis" or "cleavage" by cleaving its own C-terminus in cis to produce primary cleavage products (Furler; Palmenberg, Ann. Rev. Microbiol. 44:603-623 (1990)).

Although the mechanism is not part of the invention, the activity of 2A may involve ribosomal skipping between codons which prevents formation of peptide bonds (de Felipe et al., Human Gene Therapy 11:1921-1931 (2000); Donnelly et al., J. Gen. Virol. 82:1013-1025 (2001); although it has been considered that the domain acts more like an autolytic enzyme (Ryan et al., Virol. 173:35-45 (1989)). Studies in which the Foot and Mouth Disease Virus (FMDV) 2A coding region was cloned into expression vectors and transfected into target cells have established that FMDV 2A cleavage of artificial reporter polyproteins is efficient in a broad range of heterologous expression systems (wheat-germ lysate and transgenic tobacco plant (Halpin et al., U.S. Pat. No. 5,846, 767 (1998) and Halpin et al., The Plant Journal 17:453-459 (1999)); Hs 683 human glioma cell line (de Felipe et al., Gene Therapy 6:198-208 (1999); hereinafter referred to as "de Felipe II"); rabbit reticulocyte lysate and human HTK-143 cells (Ryan et al., EMBO J. 13:928-933 (1994)); and insect cells (Roosien et al., J. Gen. Virol. 71:1703-1711 (1990)). FMDV 2A-mediated cleavage of a heterologous polyprotein has been shown for IL-12 (p40/p35 heterodimer; Chaplin et al., J. Interferon Cytokine Res. 19:235-241 (1999)). In transfected COS-7 cells, FMDV 2A mediated the cleavage of a p40-2A-p35 polyprotein into biologically functional subunits p40 and p35 having activities associated with IL-12.

The FMDV 2A sequence has been incorporated into retroviral vectors, alone or combined with different IRES sequences to construct bicistronic, tricistronic and tetracistronic vectors. The efficiency of 2A-mediated gene expression in animals was demonstrated by Furler (2001) using recombinant adeno-associated viral (AAV) vectors encoding a-synuclein and EGFP or Cu/Zn superoxide dismutase (SOD-1) and EGFP linked via the FMDV 2A sequence. EGFP and a-synuclein were expressed at substantially higher levels from vectors which included a 2A sequence relative to corresponding IRES-based vectors, while SOD-1 was expressed at comparable or slightly higher levels. Furler also demonstrated that the 2A sequence results in bicistronic gene expression in vivo after injection of 2A-containing AAV vectors into rat substantia nigra. Recently, 2A peptides and 2A-like sequences were demonstrated to be effective in efficient translation of four cistrons using a retroviral vector (Szymczak A L et al., Nat Biotechnol. 2004 May 22(5):589-94).

For the present invention, the DNA sequence encoding a self-processing cleavage site is exemplified by viral sequences derived from a picornavirus, including but not limited to an entero-, rhino-, cardio-, aphtho- or Foot-and-Mouth Disease Virus (FMDV). In a preferred embodiment, the self-processing cleavage site coding sequence is derived from a FMDV. Self-processing cleavage sites include but are not limited to 2A and 2A-like domains (Donnelly et al., J. Gen. Virol. 82:1027-1041 (2001), expressly incorporated by reference in its entirety.

Positional subcloning of a 2A sequence between two or more heterologous DNA sequences for the inventive vector construct allows the delivery and expression of two or more genes through a single expression vector. Preferably, self processing cleavage sites such as FMDV 2A sequences provide a unique means to express and deliver from a single viral vector, two or multiple proteins, polypeptides or peptides which can be individual parts of, for example, an antibody, heterodimeric receptor or heterodimeric protein.

FMDV 2A is a polyprotein region which functions in the FMDV genome to direct a single cleavage at its own C-terminus, thus functioning in cis. The FMDV 2A domain is typically reported to be about nineteen amino acids in length (LLNFDLLKLAGDVESNPGP; SEQ ID NO: 1); (TLNFDLLKLAGDVESNPGP; SEQ ID NO: 2; Ryan et al., J. Gen. Virol. 72:2727-2732 (1991)), however oligopeptides of as few as fourteen amino acid residues (LLKLAGDVESNPGP; SEQ ID NO: 3) have been shown to mediate cleavage at the 2A C-terminus in a fashion similar to its role in the native FMDV polyprotein processing.

Variations of the 2A sequence have been studied for their ability to mediate efficient processing of polyproteins (Donnelly M L et al. 2001). Homologues and variants of a 2A sequence are included within the scope of the invention and include but are not limited to the sequences presented in Table 1, below:

TABLE 1

Table of Exemplary 2A Sequences

| | |
|---|---|
| LLNFDLLKLAGDVESNPGP | (SEQ ID NO: 1) |
| TLNFDLLKLAGDVESNPGP; | (SEQ ID NO: 2) |
| LLKLAGDVESNPGP | (SEQ ID NO: 3) |
| NFDLLKLAGDVESNPGP | (SEQ ID NO: 4) |
| QLLNFDLLKLAGDVESNPGP | (SEQ ID NO: 5) |
| APVKQTLNEDLLKLAGDVESNPGP. | (SEQ ID NO: 6) |
| VTELLYRMKRAETYCPRPLLAIHPTEARHKQKIVAP VKQTLNFDLLKLAGDVESNPGP | (SEQ ID NO: 7) |
| LLAIHPTEARHKQKIVAPVKQTLNFDLLKLAGDVES NPGP | (SEQ ID NO: 8) |
| EARHKQKIVAPVKQTLNFDLLKLAGDVESNPGP | (SEQ ID NO: 9) |

Distinct advantages of 2A sequences and variants thereof are their use in facilitating self-processing of polyproteins.

This invention includes any vector (plasmid or viral based) which includes the coding sequence for proteins or polypeptides linked via self-processing cleavage sites such that the individual proteins are expressed in equimolar or close to equimolar amounts following the cleavage of the polyprotein due to the presence of the self-processing cleavage site, e.g., a 2A domain. These proteins may be heterologous to the vector itself, to each other or to the self-processing cleavage site, e.g., FMDV.

The small size of the 2A coding sequence further enables its use in vectors with a limited packaging capacity for a coding sequence such as AAV. The utility of AAV vectors can be further expanded since the 2A sequence eliminates the need for dual promoters. The expression level of individual proteins, polypeptides or peptides from a promoter driving a single open reading frame comprising more than two coding sequences in conjunction with 2A are closer to equimolar as compared to the expression level achievable using IRES sequences or dual promoters. Elimination of dual promoters also reduces promoter interference that may result in reduced and/or impaired levels of expression for each coding sequence.

In one preferred embodiment, the FMDV 2A sequence included in a vector according to the invention encodes amino acid residues comprising LLNFDLLKLAGDVESNPGP (SEQ ID NO:1). Alternatively, a vector according to the invention may encode amino acid residues for other 2A-like regions as discussed in Donnelly et al., J. Gen. Virol. 82:1027-1041 (2001) and including but not limited to a 2A-like domain from picornavirus, insect virus, Type C rotavirus, trypanosome repeated sequences or the bacterium, Thermatoga maritima.

The invention contemplates use of nucleotide sequence variants that encode a 2A or 2A-like polypeptide, such as a nucleic acid coding sequence for a 2A or 2A-like polypeptide which has a different codon for one or more of the amino acids relative to that of the parent nucleotide. Such variants are specifically contemplated and encompassed by the present invention. Sequence variants of 2A peptides and polypeptides are included within the scope of the invention as well.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J Mol. Biol. 215: 403-410 (1990), with software that is publicly available through the National Center for Biotechnology Information (http://www.ncbi.nlm.nih.gov/), or by visual inspection (see generally, Ausubel et al., infra). For purposes of the present invention, optimal alignment of sequences for comparison is most preferably conducted by the local homology algorithm of Smith & Waterman, Adv. Appl. Math. 2: 482 (1981). See, also, Altschul, S. F. et al., 1990 and Altschul, S. F. et al., 1997.

In accordance with the present invention, also encompassed are sequence variants which encode self-processing cleavage polypeptides and polypeptides themselves that have 80, 85, 88, 89, 90, 91, 92, 93, 94, 95, 96, 97, 98, 99% or more sequence identity to the native sequence.

A nucleic acid sequence is considered to be "selectively hybridizable" to a reference nucleotide sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993. An example of high stringency conditions includes hybridization at about 42° C. in 50% formamide, 5×SSC, 5× Denhardt's solution, 0.5% SDS and 100 mg/ml denatured carrier DNA followed by washing two times in 2×SSC and 0.5% SDS at room temperature and two additional times in 0.1× SSC and 0.5% SDS at 42° C. 2A sequence variants that encode a polypeptide with the same biological activity as the 2A polypeptides described herein and hybridize under moderate to high stringency hybridization conditions are considered to be within the scope of the present invention.

As a result of the degeneracy of the genetic code, a number of coding sequences can be produced which encode the same 2A or 2A-like polypeptide. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention.

It is further appreciated that such sequence variants may or may not hybridize to the parent sequence under conditions of high stringency. This would be possible, for example, when the sequence variant includes a different codon for each of the amino acids encoded by the parent nucleotide. Such variants are, nonetheless, specifically contemplated and encompassed by the present invention.

Removal of Self-Processing Peptide Sequences

One concern associated with the use of self-processing peptides, such as 2A or 2A-like sequences is that the N terminus of the first polypeptide contains amino acids derived from the self-processing peptide, i.e. 2A-derived amino acid residues. These amino acid residues are "foreign" to the host and may elicit an immune response when the recombinant protein is expressed or delivered in vivo (i.e., expressed from a viral or non-viral vector in the context of gene therapy or administered as an in vitro-produced recombinant protein). In addition, if not removed, 2A-derived amino acid residues may interfere with protein secretion in producer cells and/or alter protein conformation, resulting in a less than optimal expression level and/or reduced biological activity of the recombinant protein. The invention includes gene expression constructs, engineered such that an additional proteolytic cleavage site is provided between a polypeptide coding sequence and the self processing cleavage site (i.e., a 2A-sequence) as a means for removal of remaining self processing cleavage site derived amino acid residues following cleavage.

Examples of additional proteolytic cleavage sites are furin cleavage sites with the consensus sequence RXK(R)R (SEQ ID NO: 10), which can be cleaved by endogenous subtilisin-like proteases, such as furin and other serine proteases within the protein secretion pathway. As shown in U.S. Ser. No.

10/831302, expressly incorporated by reference herein, the inventors have demonstrated that 2A residues at the N terminus of the first protein can be efficiently removed by introducing a furin cleavage site RAKR (SEQ ID NO:11) between the first polypeptide and the 2A sequence. In addition, use of a plasmid containing a nucleotide sequence encoding a 2A sequence and a furin cleavage site adjacent to the 2A site was shown to result in a higher level of protein expression than a plasmid containing the 2A sequence alone. This improvement provides a further advantage in that when 2A residues are removed from the N-terminus of the protein, longer 2A- or 2A like sequences or other self-processing sequences can be used. Such longer self-processing sequences such as 2A- or 2A like sequences may facilitate better equimolar expression of two or more polypeptides by way of a single promoter.

It is advantageous to employ antibodies or analogues thereof with fully human characteristics. These reagents avoid the undesired immune responses induced by antibodies or analogues originating from non-human species. To address possible host immune responses to amino acid residues derived from self-processing peptides, the coding sequence for a proteolytic cleavage site may be inserted (using standard methodology known in the art) between the coding sequence for the first protein and the coding sequence for the self-processing peptide so as to remove the self-processing peptide sequence from the expressed polypeptide, i.e. the antibody. This finds particular utility in therapeutic or diagnostic antibodies for use in vivo.

Any additional proteolytic cleavage site known in the art which can be expressed using recombinant DNA technology vectors may be employed in practicing the invention. Exemplary additional proteolytic cleavage sites which can be inserted between a polypeptide or protein coding sequence and a self processing cleavage sequence (such as a 2A sequence) include, but are not limited to a:

a). Furin cleavage site: RXK(R)R (SEQ ID. NO:10);
    b). Factor Xa cleavage site: IE(D)GR (SEQ ID. NO:12);
    c). Signal peptidase I cleavage site: e.g. LAGFATVAQA (SEQ ID. NO:13); and
    d). Thrombin cleavage site: LVPRGS (SEQ ID. NO:14).

As detailed herein, the 2A peptide sequence provides a "cleavage" site that facilitates the generation of both chains of an immunoglobulin or other protein during the translation process. In one exemplary embodiment, the C-terminus of the first protein, for example the immunoglobulin heavy chain, contains approximately 13 amino acid residues which are derived from the 2A sequence itself. The number of residual amino acids is dependent upon the 2A sequence used. As set forth above, and shown in the Examples, when a furin cleavage site sequence, e.g., RAKR (SEQ ID NO: 11), is inserted between the first protein and the 2A sequence, the 2A residues are removed from the C-terminus of the first protein. However, mass spectrum data indicates that the C-terminus of the first protein expressed from the RAKR-2A construct (RAKR discloses as SEQ ID NO: 11) contains two additional amino acid residues, RA, derived from the furin cleavage site RAKR (SEQ ID NO: 11).

Figure 14:
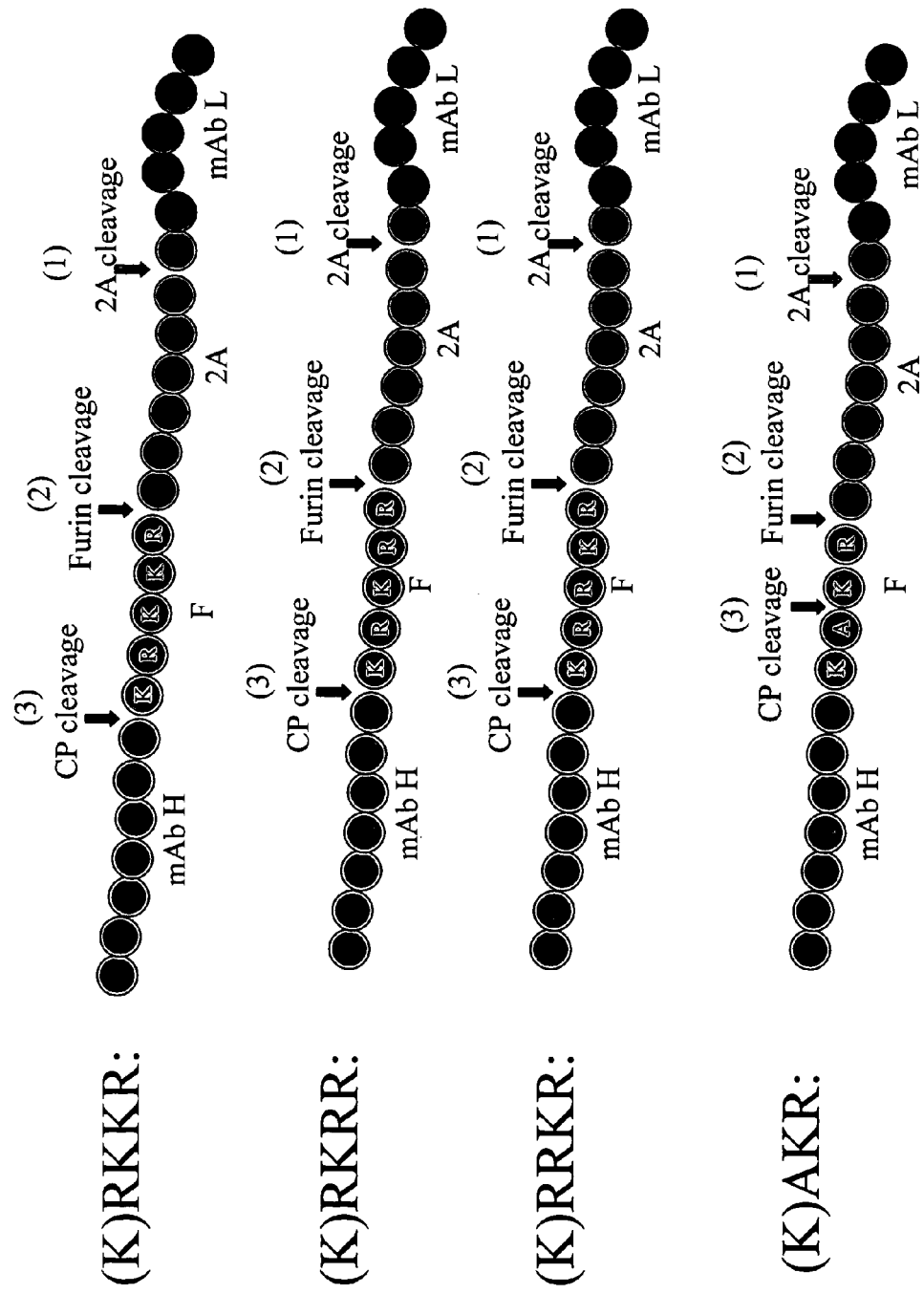
FIG. 14 is a schematic depiction of the sequential intramolecular cleavage of 2A, furin, and carboxypeptidase (CP) in human antibody H-F-2A-L constructs.
Figure 15:
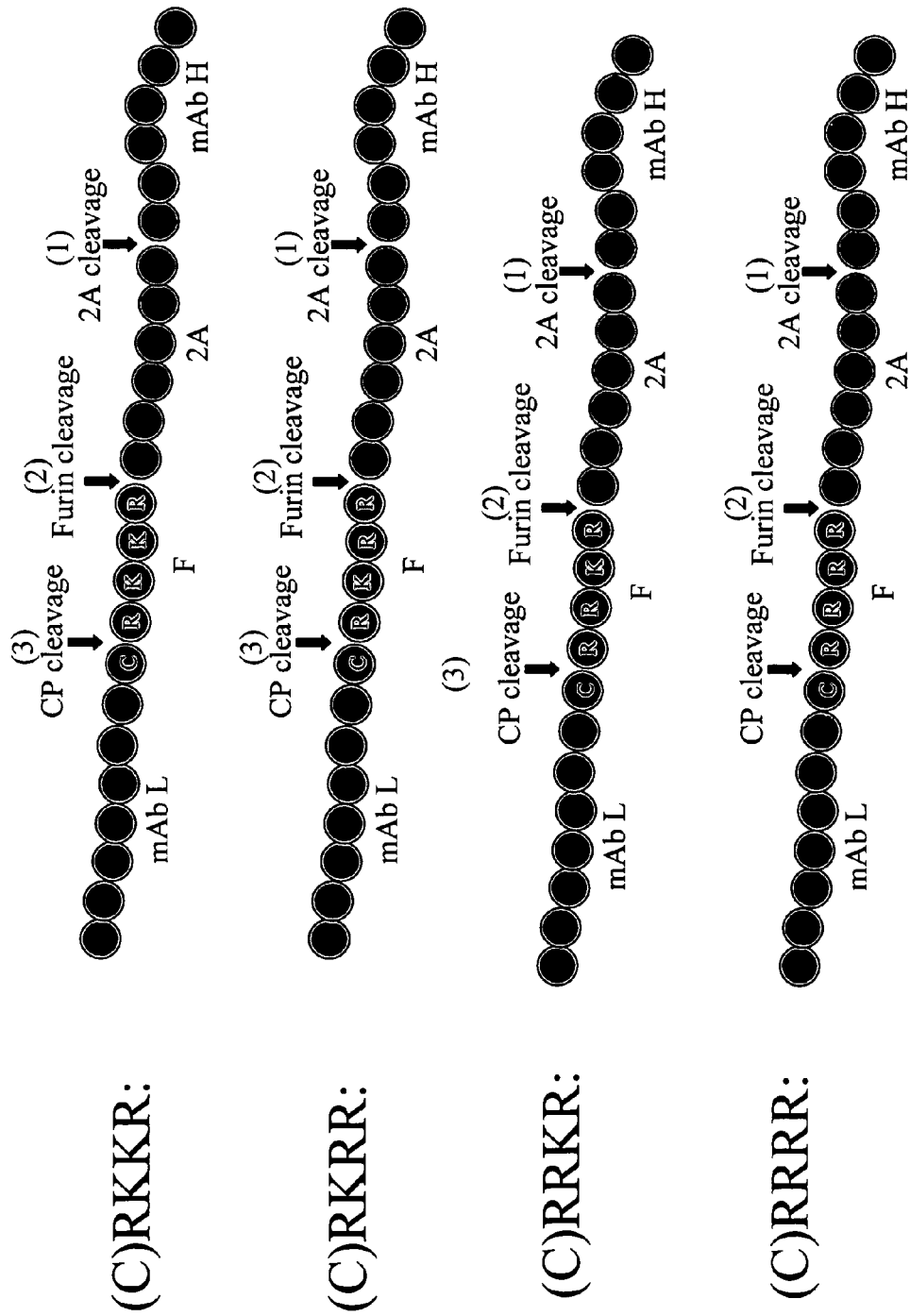
FIG. 15 is a schematic depiction of 2A, furin, and CP cleavage in human antibody L-F-2A-H constructs.

In one embodiment, the invention provides a method for removal of residual amino acids and a composition for expression of the same. A number of novel constructs have been designed that provide for removal of these additional amino acids from the C-terminus of the protein. Furin cleavage occurs at the C-terminus of the cleavage site, which has the consensus sequence RXR(K)R SEQ ID NO: 27), where X is any amino acid. In one aspect, the invention provides a means for removal of the newly exposed basic amino acid residues R or K from the C-terminus of the protein by use of an enzyme selected from a group of enzymes called carboxypeptidases (CPs), which include, but not limited to, carboxypeptidase D, E and H (CPD, CPE, CPH). Since CPs are able to remove basic amino acid residues at the C-terminus of a protein, all amino acid resides derived from a furin cleavage site which contain exclusively basic amino acids R or K, such as RKKR SEQ ID NO: 15), RKRR SEQ ID NO: 18) or RRRR (SEQ ID NO: 17), etc, can be removed by a CP. A series of immunoglobulin expression constructs that contain a 2A sequence and a furin cleavage site and which have basic amino acid residues at the C terminus have been constructed to evaluate efficiency of cleavage and residue removal. An exemplary construct design is the following: H chain—furin (e.g., RKKR (SEQ ID NO: 15), RKRR SEQ ID NO: 16), RRKR (SEQ ID NO: 18) or RRRR (SEQ ID NO: 17)-2A-L chain or L chain—furin (e.g., RKKR (SEQ ID NO: 15), RKRR SEQ ID NO: 16), RRKR (SEQ ID NO: 18) or RRRR (SEQ ID NO: 17))-2A-H chain A schematic depiction of exemplary constructs is provided in FIGS. 14 and 15, respectively.

As will be apparent to those of skill in the art, there is a basic amino acid residue (K) at the C terminus of the immunoglobulin heavy (H) chain (rendering it subject to cleavage with carboxypeptidase), while the immunoglobulin light (L) chain, terminates with a non-basic amino acid C. In one preferred embodiment of the invention, an antibody expression construct comprising a furin site and a 2A sequence is provided wherein the immunoglobulin L chain is 5' to the immunoglobulin H chain such that following translation, the additional furin amino acid residues are cleaved with carboxypeptidase.

Vectors for Use in Practicing the Invention

The present invention contemplates the use of any AAV viral vector serotype for introduction of constructs comprising the coding sequence for immunoglobulin heavy and light chains and a self processing cleavage sequence into cells so long as expression of immunoglobulin results. A large number of AAV vectors are known in the art. In generating recombinant AAV viral vectors, non-essential genes are replaced with a gene encoding a protein or polypeptide of interest. Early work was carried out using the AAV2 serotype. However, the use of alternative AAV serotypes other than AAV2 (Davidson et al (2000), PNAS 97(7)3428-32; Passini et al (2003), J. Virol 77(12):7034-40) has demonstrated different cell tropisms and increased transduction capabilities. In one aspect, the present invention is directed to AAV vectors and methods that allow optimal AAV vector-mediated delivery and expression of an immunoglobulin or other therapeutic compound in vitro or in vivo.

The vector typically comprises an origin of replication and the vector may or may not in addition comprise a "marker" or "selectable marker" function by which the vector can be identified and selected. While any selectable marker can be used, selectable markers for use in recombinant vectors are generally known in the art and the choice of the proper selectable marker will depend on the host cell. Examples of selectable marker genes which encode proteins that confer resistance to antibiotics or other toxins include, but are not limited to ampicillin, methotrexate, tetracycline, neomycin (Southern et al., J., J Mol Appl Genet. 1982;1(4):327-41 (1982)), mycophenolic acid (Mulligan et al., Science 209:1422-7 (1980)), puromycin, zeomycin, hygromycin (Sugden et al., Mol Cell Biol. 5(2):410-3 (1985)) and G418. As will be understood by those of skill in the art, expression vectors typically include an origin of replication, a promoter operably linked to the coding sequence or sequences to be expressed, as well as ribosome binding sites, RNA splice sites, a polyadenylation site, and transcriptional terminator sequences, as appropriate to the coding sequence(s) being expressed.

Reference to a vector or other DNA sequences as "recombinant" merely acknowledges the operable linkage of DNA sequences which are not typically operably linked as isolated from or found in nature. Regulatory (expression and/or control) sequences are operatively linked to a nucleic acid coding sequence when the expression and/or control sequences regulate the transcription and, as appropriate, translation of the nucleotide sequence. Thus expression and/or control sequences can include promoters, enhancers, transcription terminators, a start codon (i.e., ATG) 5' to the coding sequence, splicing signals for introns and stop codons.

Adeno-associated virus (AAV) is a helper-dependent human parvovirus which is able to infect cells latently by chromosomal integration. Because of its ability to integrate chromosomally and its nonpathogenic nature, AAV has significant potential as a human gene therapy vector. For use in practicing the present invention rAAV virions may be produced using standard methodology, known to those of skill in the art and are constructed such that they include, as operatively linked components in the direction of transcription, control sequences including transcription initiation and termination sequences, the immunoglobulin coding sequence(s) of interest and a self processing cleavage sequence. More specifically, the recombinant AAV vectors of the instant invention comprise: (1) a packaging site enabling the vector to be incorporated into replication-defective AAV virions; (2) the coding sequence for two or more polypeptides or proteins of interest, e.g., heavy and light chains of an immunoglobulin of interest; and (3) a sequence encoding a self-processing cleavage site alone or in combination with an additional proteolytic cleavage site. AAV vectors for use in practicing the invention are constructed such that they also include, as operatively linked components in the direction of transcription, control sequences including transcription initiation and termination sequences. These components are flanked on the 5' and 3' end by functional AAV ITR sequences. By "functional AAV ITR sequences" is meant that the ITR sequences function as intended for the rescue, replication and packaging of the AAV virion.

Recombinant AAV vectors are also characterized in that they are capable of directing the expression and production of recombinant immunoglobulins in target cells. Thus, the recombinant vectors comprise at least all of the sequences of AAV essential for encapsidation and the physical structures for infection of the recombinant AAV (rAAV) virions. Hence, AAV ITRs for use in the vectors of the invention need not have a wild-type nucleotide sequence (e.g., as described in Kotin, Hum. Gene Ther., 5:793-801, 1994), and may be altered by the insertion, deletion or substitution of nucleotides or the AAV ITRs may be derived from any of several AAV serotypes. Generally, an AAV vector is a vector derived from an adeno-associated virus serotype, including without limitation, AAV-1, AAV-2, AAV-3, AAV-4, AAV-5, AAV-6, AAV-7, AAV-8, etc. Preferred rAAV vectors have the wild type REP and CAP genes deleted in whole or part, but retain functional flanking ITR sequences. Table 2 illustrates exemplary AAV serotypes for use in practicing the present invention.

TABLE 2

AAV Serotypes For Use In Gene Transfer.

| Serotype | Origin | Genome Size (bp) | Homology to AAV2 | Immunity in Human Population |
|---|---|---|---|---|
| AAV-1 | Human specimen | 4718 | NT: 80% AA: 83% | NAB: 20% |
| AAV-2 | Human Genital Abortion Tissue Amnion Fluid | 4681 | NT: 100% AA: 100% | NAB: 27-53% |
| AAV-3 | Human Adenovirus Specimen | 4726 | NT: 82% AA: 88% | cross reactivity with AAV2 NAB |
| AAV-4 | African Green Monkey | 4774 | NT: 66% AA: 60% | Unknown |
| AAV-5 | Human Genital Lesion | 4625 | NT: 65% AA: 56% | ELISA: 45% NAB: 0% |
| AAV-6 | Laboratory Isolate | 4683 | NT: 80% AA: 83% | 20% |
| AAV-7 | Isolated From Heart DNA of Rhesus Monkey | 4721 | NT: 78% AA: 82% | NAB: <1:20 (~5%) |
| AAV-8 | Isolated From Heart DNA of Rhesus Monkey | 4393 | NT: 79% AA: 83% | NAB: <1:20 (~5%) |

Typically, an AAV expression vector is introduced into a producer cell, followed by introduction of an AAV helper construct, where the helper construct includes AAV coding regions capable of being expressed in the producer cell and which complement AAV helper functions absent in the AAV vector. The helper construct may be designed to down regulate the expression of the large Rep proteins (Rep78 and Rep68), typically by mutating the start codon following p5 from ATG to ACG, as described in U.S. Pat. No. 6,548,286, expressly incorporated by reference herein. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety and include those techniques within the knowledge of those of skill in the art.

Approximately 40 serotypes of AAV are currently known, however, new serotypes and variants of existing serotypes are still being identified today and are considered within the scope of the present invention. See Gao et al (2002), PNAS 99(18):11854-6; Gao et al (2003), PNAS 100(10):6081-6; Bossis and Chiorini (2003), J. Virol. 77(12):6799-810). Different AAV serotypes are used to optimize transduction of particular target cells or to target specific cell types within a particular target tissue. The use of different AAV serotypes may facilitate targeting of diseased tissue. Particular AAV serotypes may more efficiently target and/or replicate in specific target tissue types or cells. A single self-complementary AAV vector can be used in practicing the invention in order to increase transduction efficiency and result in faster onset of transgene expression (McCarty et al., Gene Ther. 2001 August;8(16):1248-54).

In practicing the invention, host cells for producing rAAV virions include mammalian cells, insect cells, microorganisms and yeast. Host cells can also be packaging cells in which the AAV rep and cap genes are stably maintained in the host cell or producer cells in which the AAV vector genome is stably maintained and packaged. Exemplary packaging and producer cells are derived from 293, A549 or HeLa cells. AAV vectors are purified and formulated using standard techniques known in the art.

The vectors of the invention typically include heterologous control sequences, including, but not limited to, constitutive promoters, such as the cytomegalovirus (CMV) immediate early promoter, the RSV LTR, the MoMLV LTR, and the PGK promoter; tissue or cell type specific promoters including mTTR, TK, HBV, hAAT, regulatable or inducible promoters, enhancers, etc. Preferred promoters include the LSP promoter (Ill et al., Blood Coagul. Fibrinolysis 8S2:23-30 (1997)), the EF1-alpha promoter (Kim et al., Gene 91(2):217-23 (1990)) and Guo et al., Gene Ther. 3(9):802-10 (1996)). Most preferred promoters include the elongation factor 1-alpha (EF1a) promoter, a phosphoglycerate kinase-1 (PGK) promoter, a cytomegalovirus immediate early gene (CMV) promoter, chimeric liver-specific promoters (LSPs), a cytomegalovirus enhancer/chicken beta-actin (CAG) promoter, a tetracycline responsive promoter (TRE), a transthyretin promoter (TTR), a simian virus 40 (SV40) promoter and a CK6 promoter. The nucleotide sequences of these and numerous additional promoters are known in the art. The relevant sequences may be readily obtained from public databases and incorporated into AAV vectors for use in practicing the present invention.

The present invention also contemplates the inclusion of a gene regulation system for the controlled expression of immunoglobulin coding sequences. Gene regulation systems are useful in the modulated expression of a particular gene or genes. In one exemplary approach, a gene regulation system or switch includes a chimeric transcription factor that has a ligand binding domain, a transcriptional activation domain and a DNA binding domain. The domains may be obtained from virtually any source and may be combined in any of a number of ways to obtain a novel protein. A regulatable gene system also includes a DNA response element which interacts with the chimeric transcription factor. This element is located adjacent to the gene to be regulated.

Exemplary gene regulation systems that may be employed in practicing the present invention include, the *Drosophila ecdysone* system (Yao et al., Proc. Nat. Acad. Sci., 93:3346 (1996)), the Bombyx ecdysone system (Suhr et al., Proc. Nat. Acad. Sci., 95:7999 (1998)), the Valentis GeneSwitch® synthetic progesterone receptor system which employs RU-486 as the inducer (Osterwalder et al., Proc Natl Acad Sci 98(22): 12596-601 (2001)); the TetÔ & RevTetÔ Systems (BD Biosciences Clontech), which employs small molecules, such as tetracycline (Tc) or analogues, e.g. doxycycline or anhydrotetracycline, to regulate (turn on or off) transcription of the target (Knott et al., Biotechniques 32(4):796, 798, 800 (2002)); ARIAD Regulation Technology which is based on the use of a small molecule to bring together two intracellular molecules, each of which is linked to either a transcriptional activator or a DNA binding protein. When these components come together, transcription of the gene of interest is activated. Ariad has two major systems: a system based on homodimerization and a system based on heterodimerization (Rivera et al., Nature Med, 2(9):1028-1032 (1996); Ye et al., Science 283: 88-91 (2000)), both of which may be employed in practicing the present invention.

Preferred gene regulation systems for use in practicing the present invention are the ARIAD Regulation Technology and the TetÔ & RevTetÔ Systems.

Delivery of Nucleic Acid Constructs Including Immunoglobulin Coding Sequences to Cells The rAAV vector constructs of the invention comprising nucleotide sequences encoding antibodies or fragments thereof in the form of self-processing recombinant polypeptides may be introduced into cells in vitro, ex vivo or in vivo for delivery of therapeutic genes to cells, e.g., somatic cells, or in the production of recombinant immunoglobulin by AAV vector-transduced cells.

The rAAV vector constructs of the invention may be introduced into cells in vitro or ex vivo using standard methodology known in the art. Such techniques include transfection using calcium phosphate, microinjection into cultured cells (Capecchi, Cell 22:479-488 (1980)), electroporation (Shigekawa et al., BioTechn., 6:742-751 (1988)), liposome-mediated gene transfer (Mannino et al., BioTechn., 6:682-690 (1988)), lipid-mediated transduction (Felgner et al., Proc. Natl. Acad. Sci. USA 84:7413-7417 (1987)), and nucleic acid delivery using high-velocity microprojectiles (Klein et al., Nature 327:70-73 (1987)).

The rAAV constructs of the invention may be introduced into cells using standard infection techniques routinely employed by those of skill in the art.

For in vitro or ex vivo expression, any cell effective to express a functional immunoglobulin may be employed. Numerous examples of cells and cell lines used for protein expression are known in the art. For example, prokaryotic cells and insect cells may be used for expression. In addition, eukaryotic microorganisms, such as yeast may be used. The expression of recombinant proteins in prokaryotic, insect and yeast systems are generally known in the art and may be adapted for antibody expression using the compositions and methods of the present invention.

Examples of cells useful for immunoglobulin expression further include mammalian cells, such as fibroblast cells, cells from non-human mammals such as ovine, porcine, murine and bovine cells, insect cells and the like. Specific examples of mammalian cells include COS cells, VERO cells, HeLa cells, Chinese hamster ovary (CHO) cells, 293 cell, NSO cells, SP20 cells, 3T3 fibroblast cells, W138 cells, BHK cells, HEPG2 cells, DUX cells and MDCK cells.

Host cells are cultured in conventional nutrient media, modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium (MEM, Sigma), RPMI 1640 (Sigma), and Dulbecco's Modified Eagle's Medium (DMEM, Sigma) are typically suitable for culturing host cells. A given medium is generally supplemented as necessary with hormones and/or other growth factors (such as insulin, transferrin, or epidermal growth factor), DHFR, salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The appropriate culture conditions for a particular cell line, such as temperature, pH and the like, are generally known in the art, with suggested culture conditions for culture of numerous cell lines provided, for example, in the ATCC Catalogue available on line at <"http://www.atcc.org/Search catalogs/ AllCollections.cfm">. A rAAV vector of the invention may be administered in vivo via any of a number of routes (e.g., intradermally, intravenously, intratumorally, into the brain, intraportally, intraperitoneally, intramuscularly, into the bladder etc.), effective to deliver rAAV in animal models or human subjects. Dependent upon the route of administration, the recombinant immunoglobulin will elicit an effect locally or systemically. The use of a tissue specific promoter 5' to the immunoglobulin open reading frame(s) results in greater tissue specificity with respect to expression of a recombinant immunoglobulin expressed under control of a non-tissue specific promoter.

For example, in vivo delivery of the recombinant AAV vectors of the invention may be targeted to a wide variety of organ types including, but not limited to brain, liver, blood vessels, muscle, heart, lung and skin. In vivo delivery of the recombinant AAV vectors of the invention may also be targeted to a wide variety of cell types based on the status of the cells, i.e. cancer cells may be targeted based on cell cycle, the hypoxic state of the cellular environment or other physiological status that deviates from the typical, or normal, physiological state of that same cell when in a non-cancerous (non-dividing or regulated dividing state under normal, physiological conditions). Examples of cell status associated promoters are the telomerase reverse transcriptase promoter (TERT) and the E2F promoter.

In the case of ex vivo gene transfer, the target cells are removed from the host and genetically modified in the laboratory using a recombinant AAV vector of the present invention and methods well known in the art.

The recombinant AAV vectors of the invention can be administered using conventional modes of administration including but not limited to the modes described above and may be in a variety of formulations which include but are not limited to liquid solutions and suspensions, microvesicles, liposomes and injectable or infusible solutions. The preferred form depends upon the mode of administration and the therapeutic application.

As the experimental results provided herein show, there are many advantages to be realized in using the inventive recombinant AAV vector constructs of the invention in immunoglobulin production in vivo, such as the administration of a single vector for long-term and sustained antibody expression in patients; in vivo expression of an antibody or fragment thereof having full biological activity; wherein the natural posttranslational modifications of the antibody takes place in human cells.

The recombinant AAV vector constructs of the present invention find further utility in the in vitro production of recombinant antibodies for use in therapy. Methods for recombinant protein production are well known in the art and may be utilized for expression of recombinant antibodies using the self processing cleavage site-containing vector constructs described herein.

In one aspect, the invention provides methods for producing a recombinant immunoglobulin or fragment thereof, by introducing an AAV vector such as described above into a cell to obtain an AAV-infected cell, wherein the vector comprises in the 5' to 3' direction: a promoter operably linked to the coding sequence for an immunoglobulin heavy or light chain or fragment thereof, a self processing sequence such as a 2A or 2A-like sequence and the coding sequence for an immunoglobulin heavy or light chain or a fragment thereof, wherein the self processing cleavage sequence is inserted between the first and second immunoglobulin coding sequences. It will be appreciated that the coding sequence for either the immunoglobulin heavy chain or the coding sequence for the immunoglobulin light chain may be 5' to the 2A sequence (i.e. first) in a given AAV construct.

In a related aspect, the invention provides a method for producing a recombinant immunoglobulin or fragment thereof, by introducing an AAV vector such as described above into a cell, wherein the AAV vector further comprises an additional proteolytic cleavage site between the first and second immunoglobulin coding sequences. A preferred additional proteolytic cleavage site is a furin cleavage site with the consensus sequence RXK(R)R (SEQ ID NO:10).

In one exemplary aspect of the invention, AAV vector introduction to a cell in vitro is followed by one or more of the following steps:
(1) culturing the transfected cell under conditions for selecting a cell expressing the immunoglobulin or fragment thereof;
(2) measuring expression of the immunoglobulin or the fragment thereof; and
(3) collecting the immunoglobulin or the fragment thereof.

In another exemplary aspect of the invention, AAV vector administration to a patient in vivo is followed by one or more of the following steps:
(1) collecting serum, plasma or other tissue sample from the patient;
(2) measuring the expression level of the immunoglobulin or the fragment thereof; and in
(3) adjusting the therapeutic regimen dependent upon the detected level of immunoglobulin or the fragment thereof.

Another aspect of the invention provides a cell for expressing a recombinant immunoglobulin or a fragment thereof, wherein the cell comprises an AAV vector for the expression of two or more immunoglobulin chains or fragments thereof, a promoter operably linked to a first coding sequence for an immunoglobulin chain or fragment thereof, a self processing cleavage sequences, such as a 2A or 2A-like sequence, and a second coding sequence for an immunoglobulin chain or a fragment thereof, wherein the self processing cleavage sequence is inserted between the first and the second coding sequences. In a related aspect, the cell comprises an AAV vector as described above wherein the expression vector further comprises an additional proteolytic cleavage site between the first and second immunoglobulin coding sequences. A preferred additional proteolytic cleavage site is a furin cleavage site with the consensus sequence RXK(R)R (SEQ ID NO:10).

In yet another aspect, the invention provides a method for producing a recombinant immunoglobulin molecule in vivo by transducing a host cell with an AAV vector according to the invention, where the first immunoglobulin coding sequence and the second immunoglobulin coding sequence are expressed in a substantially equimolar ratio. In some applications, the methods of the invention find utility in the treatment of cancer or in the preparation of recombinant antibody vaccines.

Antibody Production

The nucleotide sequence encoding the first or second chain for an antibody or immunoglobulin or a fragment thereof includes a heavy chain or a fragment thereof for an IgG, IgM, IgD, IgE or IgA. The sequence encoding the chain for an antibody or immunoglobulin or a fragment thereof also includes the light chain or a fragment thereof for an IgG, IgM, IgD, IgE or IgA. Genes for whole antibody molecules as well as modified or derived forms thereof, include fragments like Fab, single chain Fv(scFv) and F(ab')$_2$. The antibodies and fragments can be animal-derived, human-mouse chimeric, humanized, DeImmunizedÔ or fully human. The antibodies can be bispecific and include but are not limited to diabodies, quadroma, mini-antibodies, ScBs antibodies and knobs-into-holes antibodies.

The production and recovery of the antibodies themselves can be achieved in various ways known in the art (Harlow et al., "Antibodies, A Laboratory Manual", Cold Spring Harbor Lab, (1988)).

In practicing the invention, the production of an antibody or variant (analogue) thereof using recombinant DNA technology can be achieved by culturing a modified recombinant host cell under culture conditions appropriate for the growth of the host cell and the expression of the coding sequences. In order to monitor the success of expression, the antibody levels with respect to the antigen may be monitored using standard techniques such as ELISA, RIA and the like. The antibodies are recovered from the culture supernatant using standard techniques known in the art. Purified forms of these antibodies can, of course, be readily prepared by standard purification techniques, preferably including affinity chromatography via protein A, protein G or protein L columns, or with respect to the particular antigen, or even with respect to the particular epitope of the antigen for which specificity is desired. Antibodies can also be purified with conventional chromatography, such as an ion exchange or size exclusion column, in conjunction with other technologies, such as ammonia sulfate precipitation and size-limited membrane filtration. Preferred expression systems are designed to include signal peptides so that the resulting antibodies are secreted into the culture medium or supernatant, however, intracellular production is also possible.

The production and selection of antigen-specific fully human monoclonal antibodies from mice engineered with human Ig loci, has previously been described (Jakobovits A. et al., Advanced Drug Delivery Reviews Vol. 31, pp: 33-42 (1998); Mendez M, et al., Nature Genetics Vol. 15, pp: 146-156 (1997); Jakobovits A. et al., Current Opinion in Biotechnology Vol. 6, No. 5, pp: 561-566 (1995); Green L, et al., Nature Genetics Vol. 7, No. 1, pp: 13-21(1994).

It will be understood that the AAV vectors of the invention which comprise the coding sequence for a self-processing peptide alone or in combination with an additional coding sequence for a proteolytic cleavage site find utility in the expression of recombinant immunoglobulins or fragments thereof in any cell type in vitro and following administration by any of a number of routes in vivo, a number of which are known in the art and examples of which are described herein. One of skill in the art may easily adapt the vectors of the invention for use in any protein expression system.

The objects of the invention have been achieved by a series of experiments, some of which are described by way of the following non-limiting examples.

EXAMPLES

Example 1

Construction of AAV 2A Expression Constructs

AAV vectors encoding full length heavy and light chains of a rat anti-FLK-1 monoclonal antibody and a fully human anti-KDR monoclonal antibody with self processing cleavage sequences (2A) were constructed as shown in FIG. 1A. The variable and constant regions of the antibody heavy and light chains were cloned from cDNA of the parental hydridoma cells using the Polymerase Chain Reaction (PCR). The cDNAs were synthesized with reverse transcriptase from total RNA isolated from the hydridoma cells using Qiagen's total RNA purification kit. The nucleotide sequences of the monoclonal antibodies were analyzed using an automatic sequencing system (Applied Biosystems) and consensus sequences were obtained from the sequencing data derived from multiple independent PCR reactions.

The DNA fragments that encode the heavy chain, 2A sequence and antibody light chain of either a rat mAb or human mAb were linked together by PCR extension. Artificial FMDV 2A oligo nucleotides were synthesized based on the 2A peptide sequence APVKQTLNFDLLKLAGDVESN-PGP (SEQ ID NO: 6). The heavy and light chain fragments were amplified from the cloned plasmids that encode the full-length antibody heavy and light chains respectively. During the PCR, an EcoR I restriction endonucleotidase site was added to the 5' end of the heavy chain and the 3' end of the light chain. The fused heavy chain-2A-light chain DNA fragment was digested with EcoR I and purified from agarose gel. The purified DNA fragment was inserted into an AAV plasmid backbone flanked with EcoR I sites using T4 DNA ligase. AAV constructs containing an EF1-alpha promoter or a CAG promoter driving expression of the antibody heavy chain-2A sequence-light chain were prepared. In variant forms, a native signal peptide (leader) was included in the heavy or light chain, respectively, to facilitate secretion of the polypeptides upon synthesis.

Example 2

Construction of AAV 2A Expression Constructs with a Furin Cleavage Site

Antibody heavy chains expressed from the H-2A-L constructs described above carry residual amino acids at their C-terminus which remain from the 2A sequence following self cleavage. To further optimize the expression system and eliminate amino acids/sequences that are foreign to the host, a vector was constructed which includes a protease cleavage site between the first polypeptide, i.e. the immunoglobulin heavy chain in this exemplary construct, and the 2A sequence. The cleavage site used was RAKR (SEQ ID NO: 11), which belongs to the category of furin consensus cleavage sequences. The antibody heavy chain-furin cleavage site-2A-light chain DNA fragments for both the rat antibody FLK-1 antibody and the human anti-KDR antibody were fused by PCR and were cloned into AAV backbone plasmids, respectively, using the method described in Example 1. The constructs consist of in the 5' to 3' direction: a 5' AAV ITR, a promoter, the coding sequence for an antibody heavy chain (H), an additional proteolytic cleavage site coding sequence (e.g., in this case a furin cleavage site coding sequence), the coding sequence for a self processing cleavage sequence (n this case a 2A sequence), the coding sequence for an antibody light chain (L), and a polyA sequence (e.g., CAG H-F2A-L) (FIG. 1B).

Example 3

AAV Production and Expression of a Rat IgG From AAV H-2A-L and AAV H-F-2A-L Viruses In Vitro The current invention provides AAV vectors that produce high levels of biologically active antibodies by use of a single promoter for expression of anti-FLK-1 heavy chain-2A-light chain (H-2A-L) or anti-FLK-1 heavy chain-furin cleavage site-2A-light chain (H-F-2A-L), allowing the antibody heavy and light chains to be expressed as a single open reading frame within the same cell. The AAV vectors were produced in 293 cells. AAV DNA was purified using a plasmid DNA mega purification kit (Qiagen). 293 cells were grown in 15 cm tissue culture plates until subconfluence, followed by co-transfection with an AAV6 or AAV8 vector plasmid (AAV H-2A-L or AAV H-F-2A-L), a Rep/Cap plasmid for AAV6 or AAV8, and an adenovirus helper plasmid. After transfection, AAV viruses were purified from 293 cell lysates by double CsCl gradient centrifugations, followed by extensive dialysis against PBS over night. The physical titers of rAAV viruses were determined by dot blot analysis with the probes using AAV plasmids as templates. AAV vectors were prepared for the full length rat anti-FLK-1 mAb using: an AAV6 backbone and a CAG promoter (AAV6 CAG H2AL), an AAV8 backbone and an EF1-alpha promoter (AAV8 EF1 alpha H2AL), an AAV8 backbone and a CAG promoter (AAV8 CAG H2AL), and an AAV8 backbone with a CAG promoter where the vector further includes a Furin cleavage site as an exemplary additional proteolytic cleavage site (AAV8 CAG H-F-2A-L).

To express a monoclonal antibody from the various AAV vectors in vitro, 293 or HuH7 cells were cultured in 6 well plates. The cells were infected with AAV vectors by adding each respective purified AAV vector to the culture plates with or without Adenovirus-5 (as a helper). After 48 hours, cell culture supernatants were collected and IgG1 was quantified. A rat IgG1 ELISA kit from Bethyl Laboratories was used for rat IgG1 analyses. Rat monoclonal antibody protein was detected in cell culture supernatants of 293 or HuH7 cells infected by $1\times10^5$ of the AAV6 CAG H2AL, AAV8 EF1 alpha H2AL, AAV8 CAG H2AL, and AAV8 CAG H-F-2A-L viruses (Table 3), respectively, but not in the supernatants taken from control wells that were not infected by the antibody-encoding AAV viruses (as described above).

The results presented in Table 3 demonstrate that full length antibody can be expressed in vitro using AAV virus vectors of various serotypes (e.g., AAV6 and AAV8) wherein the antibody heavy and light chains are expressed as a single open reading frame using a self-processing sequence such as 2A.

TABLE 3

| Rat IgG1 expression in vitro following AAV infection ($1 \times 10^5$ vp/well) | | | |
|---|---|---|---|
| | Antibody Concentration (µg/ml) | | |
| Virus | (+Adeno) | (−Adeno) | Cells |
| AAV6 CAG H-2A-L | 0.59 | 0.23 | HuH7 |
| AAV8 EF1 aplha H-2A-L | 0.163 | 0.022 | 293T |
| AAV8 CAG H-F-2A-L | 5.22 | 0.547 | HuH7 |

TABLE 3-continued

| Rat IgG1 expression in vitro following AAV infection ($1 \times 10^5$ vp/well) | | | |
|---|---|---|---|
| | Antibody Concentration (µg/ml) | | |
| Virus | (+Adeno) | (−Adeno) | Cells |
| No AAV | 0 | 0 | 293T |
| No AAV | 0 | 0 | HuH7 |

Example 4

Expression of Rat Anti-FLK-1 mAb from an AAV H2AL or AAV H-F-2A-L Vectors in Nude Mice.

This experiment demonstrates that high antibody serum levels can be achieved in mice following administration of AAV viral vectors that encode monoclonal antibodies wherein expression occurs by use of a single promoter and a self processing cleavage sequence located between the antibody heavy and light chain coding sequence (exemplified herein by 2A). High level antibody expression was shown using a rat anti-FLK-1 mAb heavy-2A-light chain (H-2A-L) and a mAb heavy chain-furin cleavage site-2A-light chain (H-F-2A-L) AAV vector, respectively.

analyzed for antibody levels using a rat IgG1 kit as described in Example 3.

Figure 2:
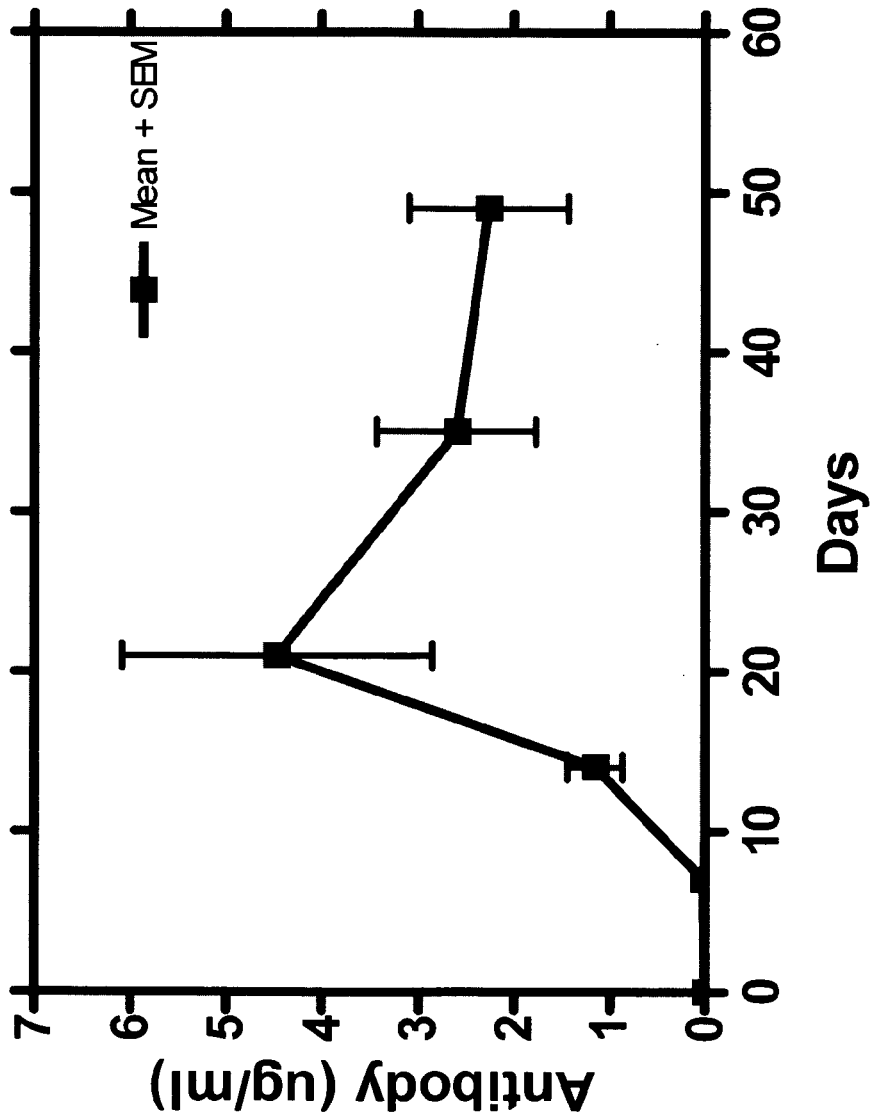
FIG. 2 depicts the in vivo antibody expression level (μg/ml) in mouse serum following intramuscular (i.m.) injection of $2 \times 10^{11}$ vp (viral particles) of an AAV6 vector encoding the antibody heavy chain, a 2A sequence, and the antibody light chain (H2AL) for a rat anti-FLK-1 antibody (DC101) where the antibody is expressed under the control of a hybrid promoter/enhancer that consists of cytomegalovirus promoter and enhancer sequences, chicken beta-actin (CAG) promoter and enhancer sequences and a chimeric intron.

As shown in FIG. 2, administration of $2\times10^{11}$ vp of an AAV6 CAG rat mAb H-F-L viral vector by intramuscular (i.m.) injection resulted in antibody levels in mouse serum of up to 4.5 µg/ml, with persistent expression up to at least Day 50.

Figure 3:
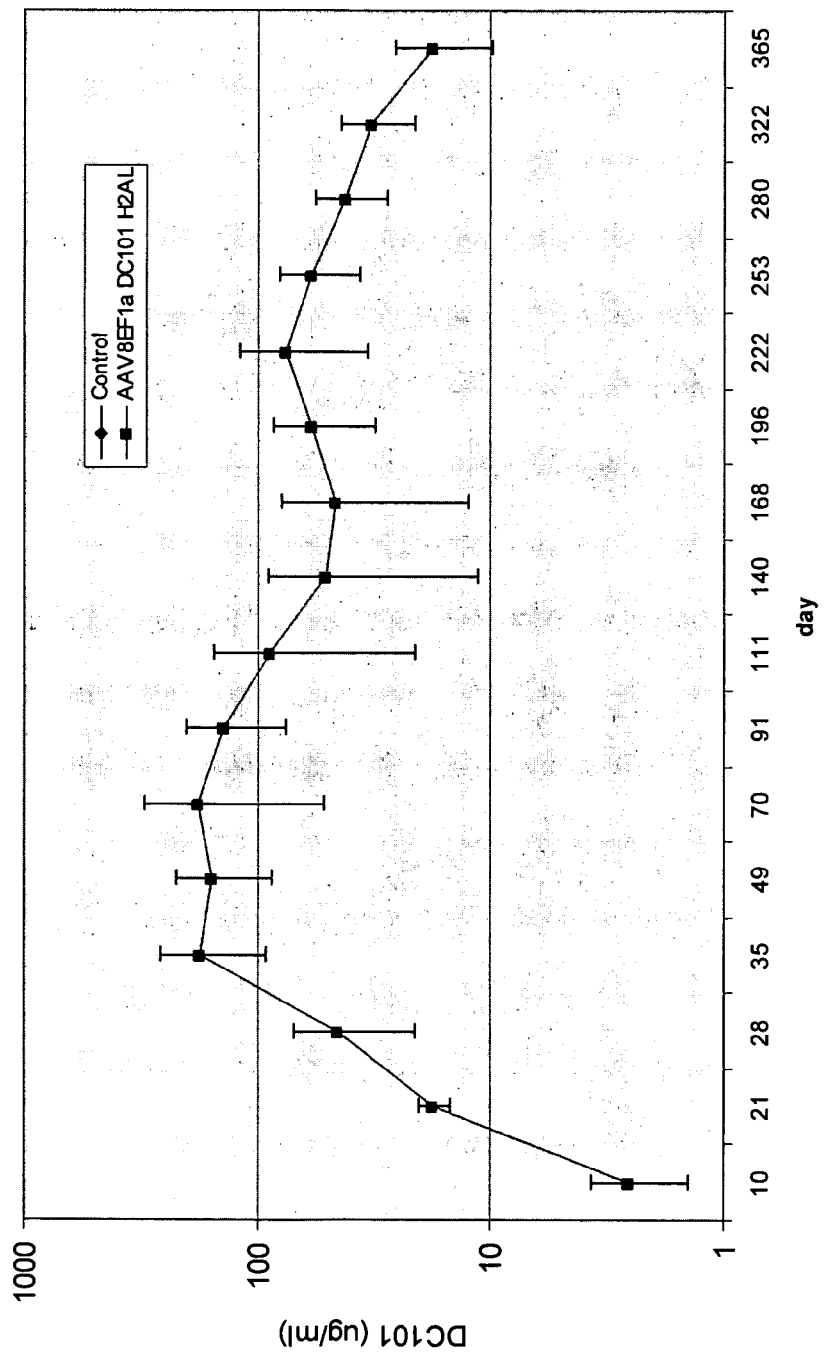
FIG. 3 depicts the in vivo antibody (IgG1) expression level (µg/ml) in mouse serum following portal vein (pv) injection of $4 \times 10^{11}$ vp of an AAV8 vector encoding the antibody heavy chain, a 2A sequence, and the antibody light chain (H2AL) for a rat anti-FLK-1 antibody (DC101) where the antibody is expressed under control of an elongation factor 1-alpha (EF1a) promoter.

As shown in FIG. 3, administration of $4\times10^{11}$ vp of an AAV8 EF1 alpha rat mAb H-2A-L viral vector via portal vein (pv) injection resulted in IgG1 levels about 100 µg/ml in mouse serum where the IgG1 persisted for greater than 200 days following injection, and IgG1 levels of more than 30 µg/ml were observed for greater than 320 days.

Figure 4:
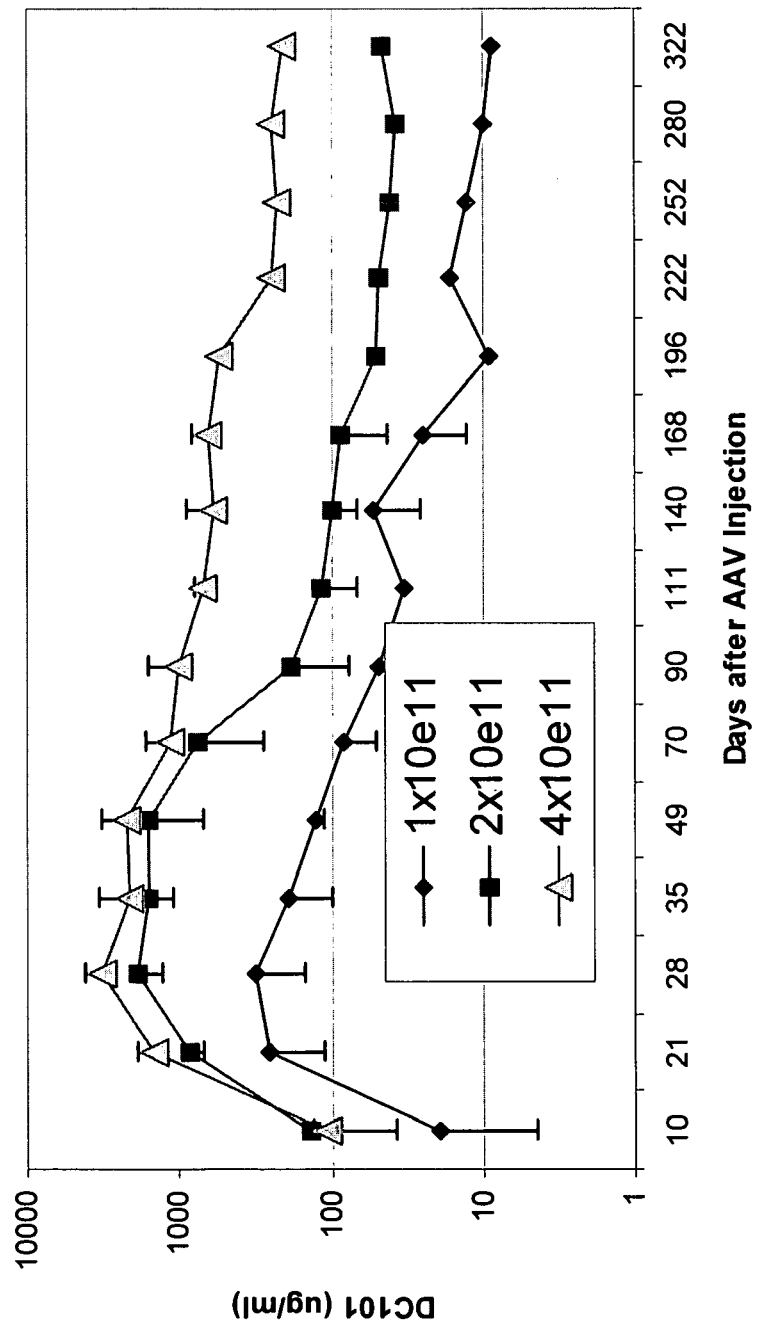
FIG. 4 depicts the in vivo antibody (DC101) expression level (µg/ml) in mouse serum following portal vein (pv) injection of $1 \times 10^{11}$ vp, $2 \times 10^{11}$ vp or $4 \times 10^{11}$ vp of an AAV8 vector encoding the antibody heavy chain, a 2A sequence, and the antibody light chain (H2AL) for a rat anti-FLK-1 antibody (DC101) where the antibody is expressed under the control of a hybrid promoter/enhancer that consists of cytomegalovirus promoter and enhancer sequences, chicken beta-actin (CAG) promoter and enhancer sequences and a chimeric intron.

As shown in FIG. 4, administration of $1\times10^{11}$ vp, $2\times10^{11}$ vp or $4\times10^{11}$ vp of an AAV8 CAG rat mAb H-2A-L viral vector via portal vein injection gave high levels of dose-dependent IgG expression in mouse serum at all 3 doses tested ($1\times10^{11}$ vp, $2\times10^{11}$ vp and $4\times10^{11}$ vp). In animals treated with $4\times10^{11}$ vp, serum mAb (IgG) levels reached more than 2 mg/ml at day 28, remained higher than 500 µg/ml for greater than three months and persisted at levels of more than 210 µg/ml for greater than 320 days.

Figure 5:
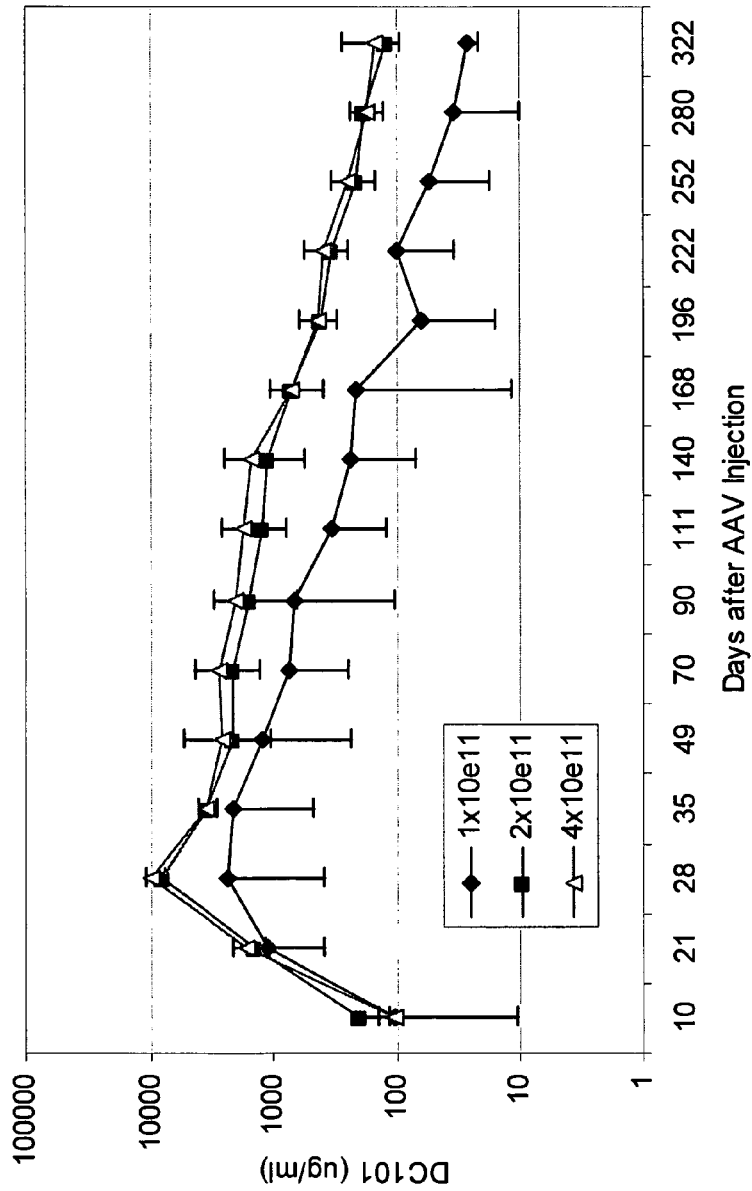
FIG. 5 depicts the in vivo antibody (DC101) expression level (µg/ml) in mouse serum following portal vein (pv) injection of $1 \times 10^{11}$ vp, $2 \times 10^{11}$ vp or $4 \times 10^{11}$ vp of an AAV8 vector encoding the antibody heavy chain, a furin cleavage site, a 2A sequence, and the antibody light chain (HF2AL) for a rat anti-FLK-1 antibody (DC101) where the antibody is expressed under the control of a hybrid promoter/enhancer that consists of cytomegalovirus promoter and enhancer sequences, chicken beta-actin (CAG) promoter and enhancer sequences and a chimeric intron.

The highest antibody expression level in the first 100 days was observed in mouse serum taken from animals injected with an AAV8 viral vector encoding a rat mAb under control of a CAG promoter where the vector also included a furin cleavage sequence and a 2A sequence. As shown in FIG. 5, administration of AAV8 CAG rat mAb H-F-2A-L virus via portal vein injection gave extremely high levels of antibody expression in mouse serum with dose-dependent expression. For the groups of mice injected with $2\times10^{11}$ and $4\times10^{11}$ viral particles/mouse, about 10 mg/ml of rat mAb was detected at Day 28 and a persistent expression level of more than 1 mg/ml was detected for more than three months following AAV viral vector injection, and IgG1 levels of more than 100 µg/ml were present at 320 days.

These results demonstrate that full-length antibodies can be expressed at extremely high levels in vivo from an AAV vector driving a single open reading frame of an immunoglobulin heavy and light chain cDNA where the vector contains a single promoter together with a self processing cleavage sequence (such as 2A) located between the two chains. Addition of a proteolytic cleavage site (e.g., a Furin cleavage site) between the 5' coding sequence and the 2A sequence not only facilitates removal of 2A residues from the first polypeptide, but resulted in enhanced serum monoclonal antibody (mAb) expression levels in vivo. This methodology is described in detail in U.S. Ser. No. 10/831302 and U.S. Ser. No. 10/831304, each of which is expressly incorporated by reference in their entirety herein. The results of previous studies were confirmed in that the serum levels of mAb detected in vivo during the first 100 days was consistently higher when an AAV8 vector which includes both a self processing cleavage sequence (such as 2A) and an additional proteolytic cleavage site (e.g., a Furin cleavage site) between the 5' coding sequence and the 2A sequence was used, e.g. an AAV8-CAG-H-F-2A-L vector.

Example 5

Inhibition of Tumor Growth In Vivo by Rat Anti-FLK-1 MAB Delivered by AAV8 CAG Vector with 2A Self-Processing Sequence and a Furin Clevage Site.

Further studies were done to evaluate the biological activity of the monoclonal antibodies expressed using AAV vectors of the current invention. In these studies, AAV mediated gene transfer of a nucleotide sequence encoding a full length rat anti-FLK-1 mAb was shown to suppress tumor growth in mouse tumor models in vivo.

Figure 6:
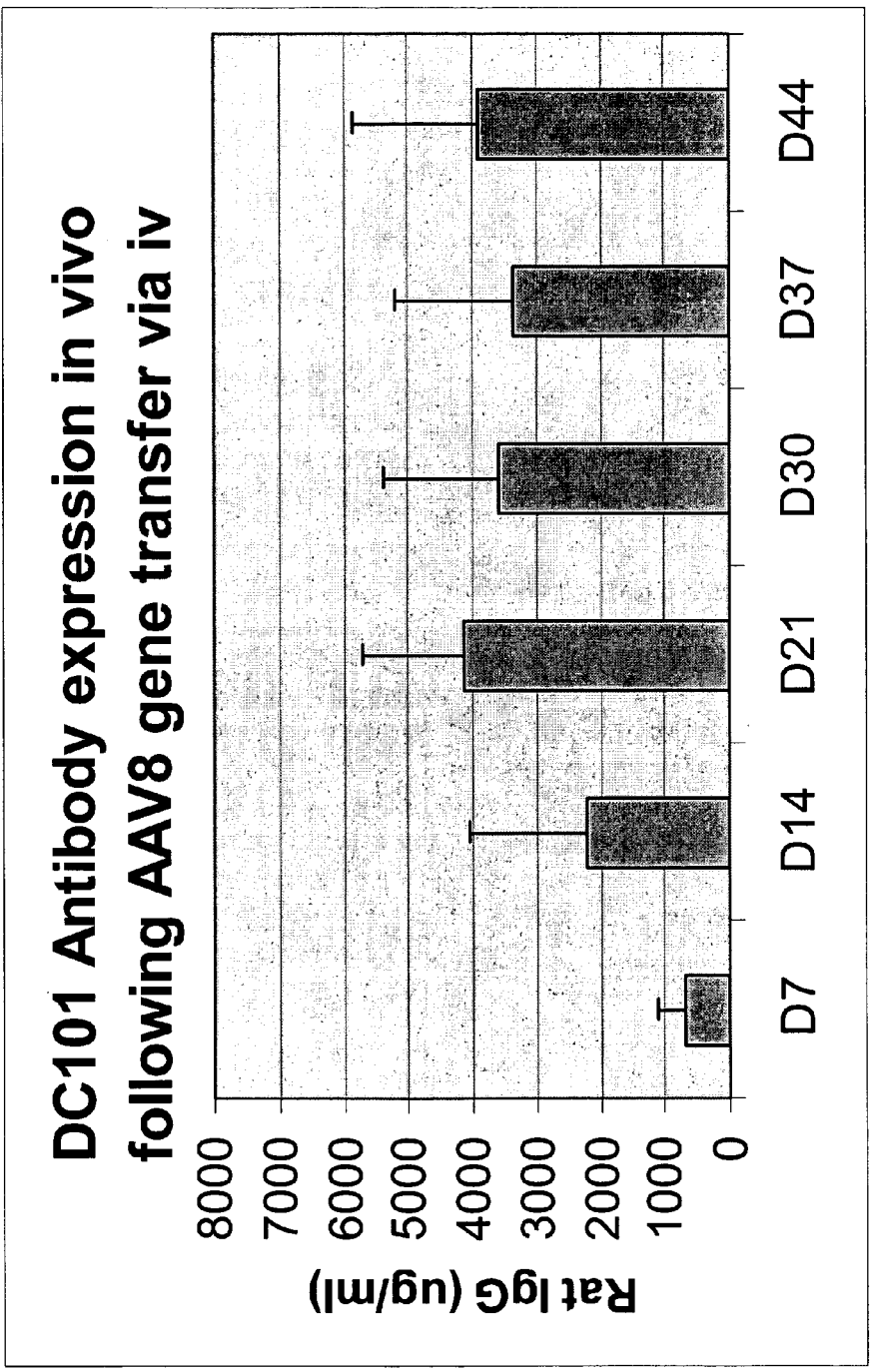
FIG. 6 depicts the in vivo antibody (rat IgG) expression level (µg/ml) in mouse serum at days 7, 14, 21, 30, 37 and 44, following intravenous (iv) injection of $2 \times 10^{11}$ vp of an AAV8 vector encoding the antibody heavy chain, a furin cleavage site, a 2A sequence, and the antibody light chain (HF2AL) for a rat anti-FLK-1 antibody (DC101) where the antibody is expressed under the control of a hybrid promoter/enhancer that consists of cytomegalovirus promoter and enhancer sequences, chicken beta-actin (CAG) promoter and enhancer sequences and a chimeric intron.
Figure 7:
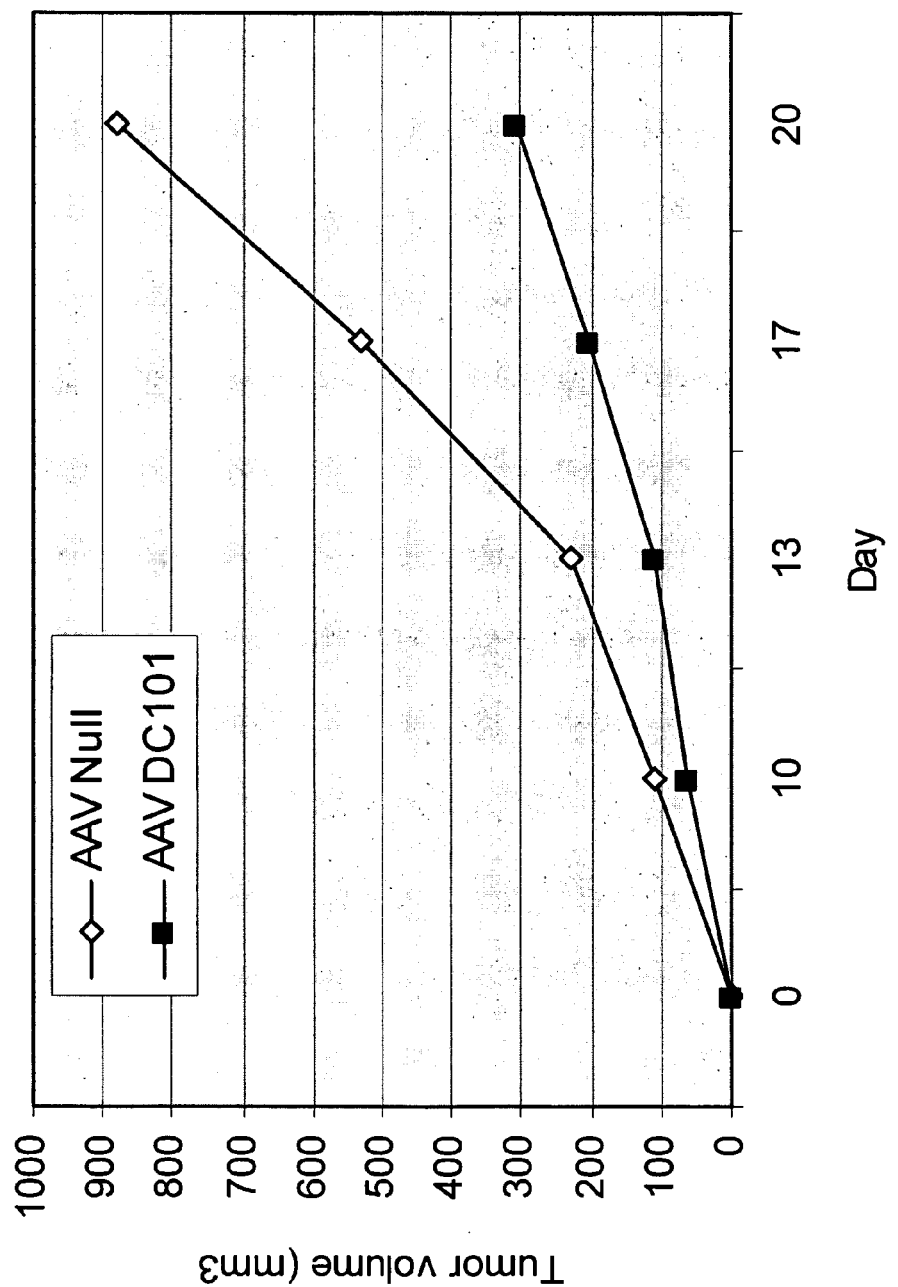
FIG. 7 shows that AAV8-mediated expression of a rat anti-FLK-1 antibody (DC101) in a B16F10 tumor model reduced B16F10 tumor growth relative to that observed in mock-treated controls up to Day 24 following intravenous (iv) injection of $2 \times 10^{11}$ vp of an AAV8 vector encoding the antibody heavy chain, a furin cleavage site, a 2A sequence, and the antibody light chain (HF2AL) for a rat anti-FLK-1 antibody (DC101).
Figure 8:
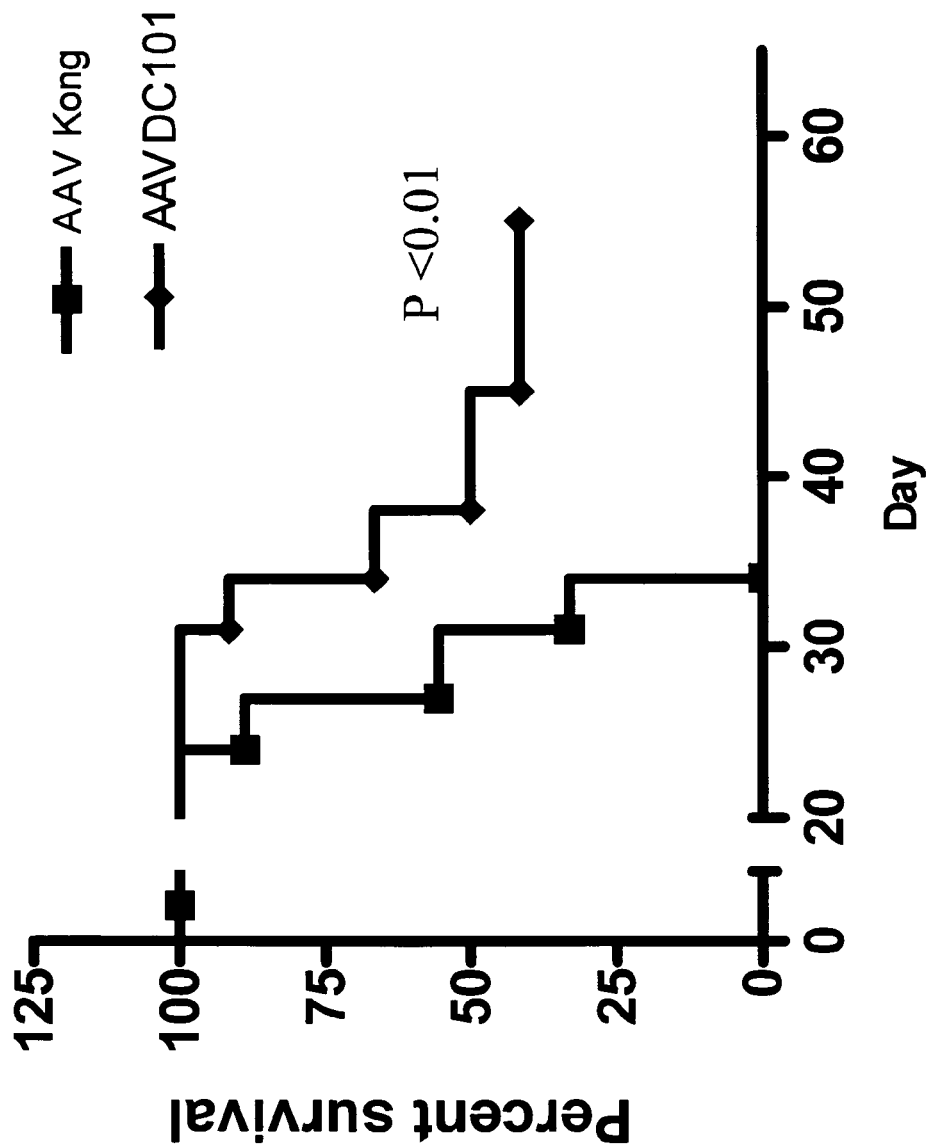
FIG. 8 shows that AAV8-mediated expression of a rat anti-FLK-1 antibody (DC101) in animals challenged with a B16F10 tumor led to increased survival of such animals relative to mock-treated control animals. Four animals that had received an intravenous (iv) injection of $2 \times 10^{11}$ vp of an AAV8 vector expressing the antibody heavy chain, a 2A sequence, and the antibody light chain (HF2AL) of a rat anti-FLK-1 antibody (DC101) survived long term compared to mock control treated animals that all died by day 32 due to large tumor burden.
Figure 9:
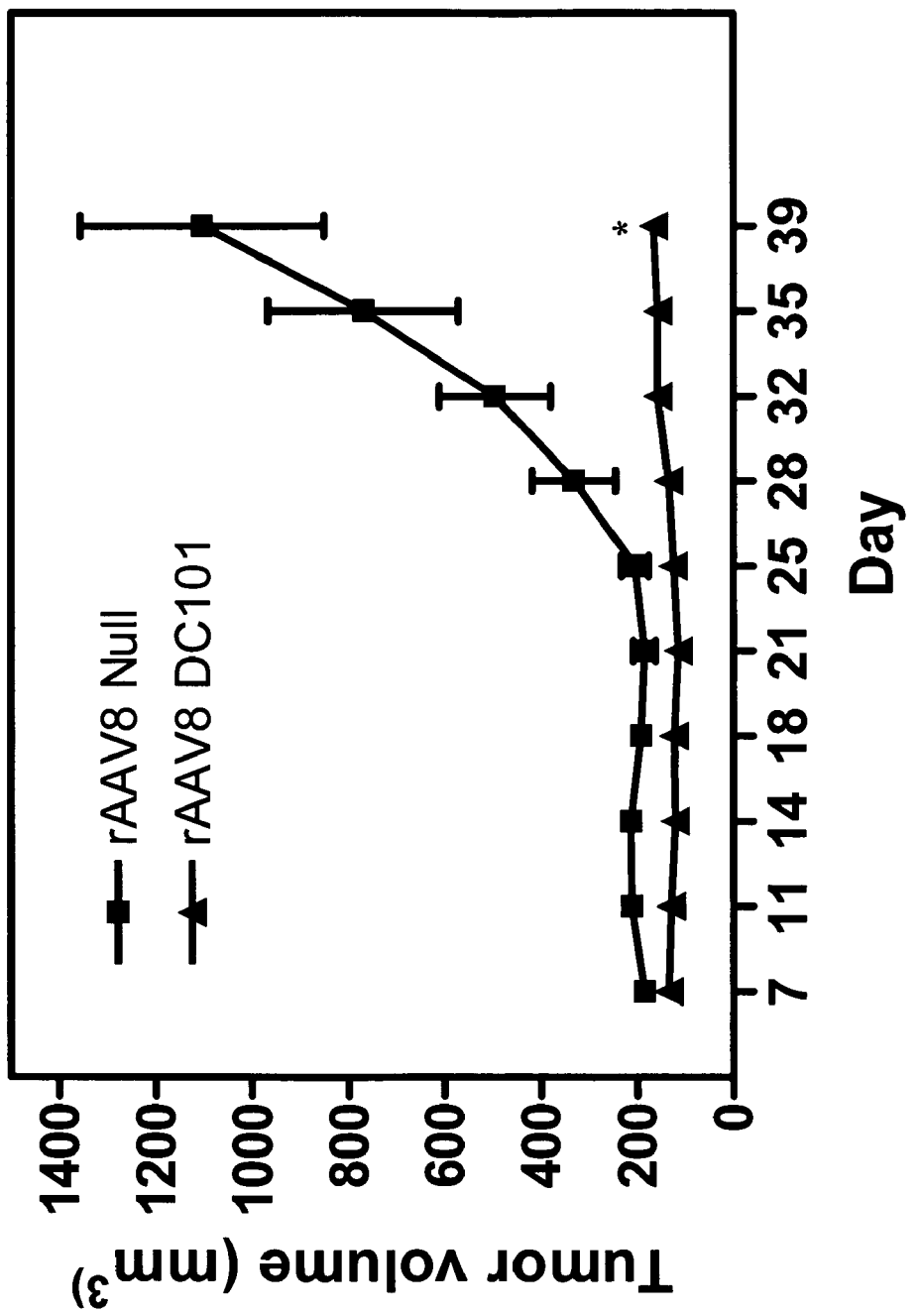
FIG. 9 shows that AAV8-mediated expression of a rat anti-FLK-1 antibody (DC101) in a U87 glioma tumor model results in reduced U87 tumor growth relative to that observed in mock-treated controls following intravenous (iv) injection of $2 \times 10^{11}$ vp of an AAV8 vector encoding the antibody heavy chain, a furin cleavage site, a 2A sequence, and the antibody light chain (HF2AL) of a rat anti-FLK-1 antibody (DC101).
Figure 10:
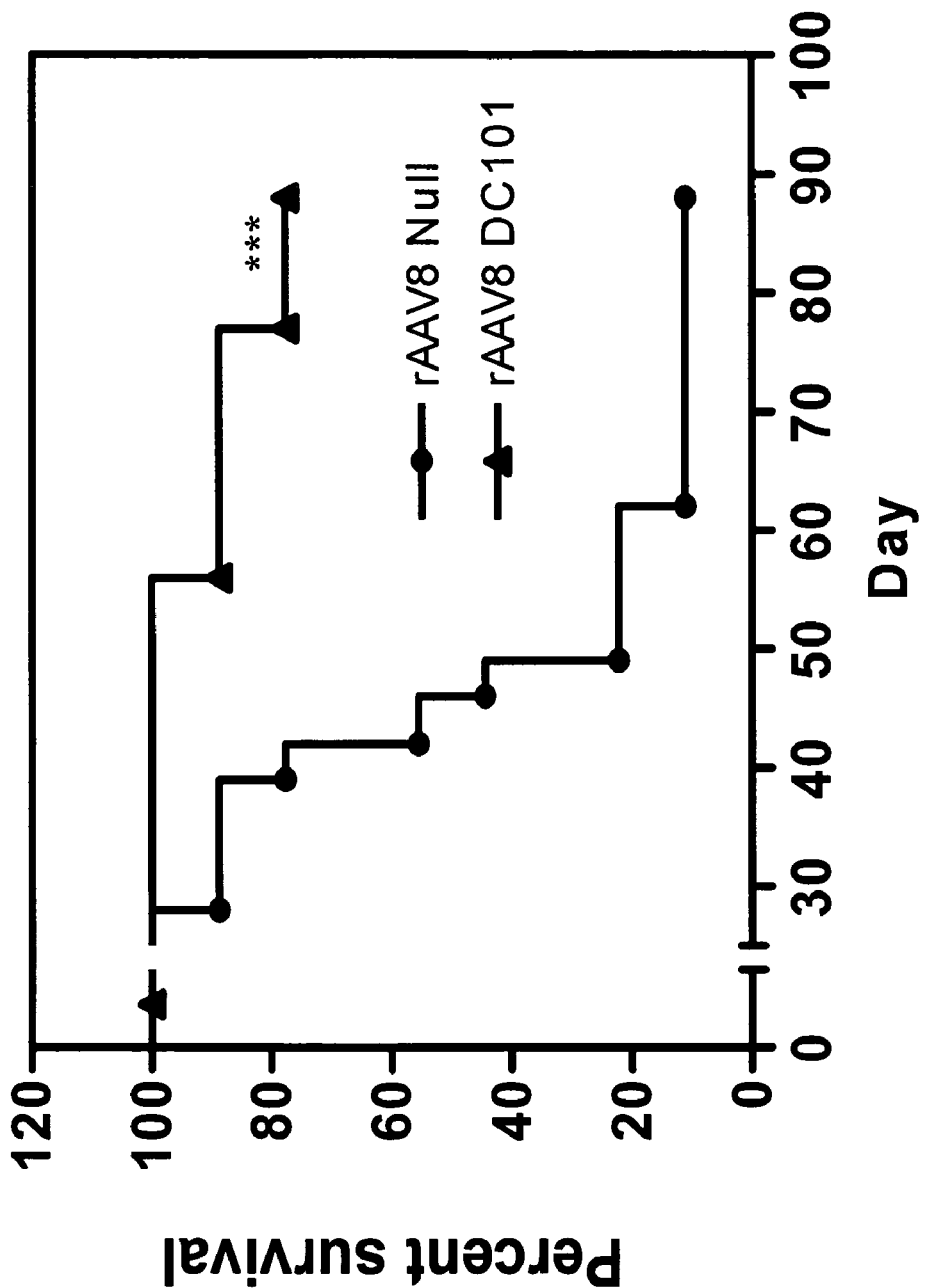
FIG. 10 shows that AAV8-mediated expression of a rat anti-FLK-1 antibody (DC101) in a U87 glioma tumor model results in increased survival relative to that observed for mock-treated controls following intravenous (iv) injection of $2 \times 10^{11}$ vp of an AAV8 vector encoding the antibody heavy chain, a furin cleavage site, a 2A sequence, and the antibody light chain (HF2AL) of a rat anti-FLK-1 antibody (DC101).

The AAV8-CAG-H-F-2A-L vector was produced in 293 cells as described in Example 3. Viral infectivity was confirmed by mAb expression in HuH7 cells following AAV infection. AAV8 CAG H-F-2A-L or AAV8 control vector ($2 \times 10^{11}$ viral particles/mouse) was administered intravenously into nude mice. Mice were bled weekly to determine the rat antibody serum levels by ELISA (Bethyl Laboratories, as described above). At Day 23 following vector administration, the mice were injected subcutaneously with either $1 \times 10^5$ B16F10 melanoma cells or $5 \times 10^6$ of U87 glioma cells (mixed with Madrigal at a 1:1 volume) and tumor size was measured twice a week using a caliper. High serum mAb concentrations were detected in the mice treated with AAV8 CAG rat mAb H-F-2A-L virus (FIG. 6). No rat mAb were detected in the serum from control mice. In mice injected with AAV8 CAG rat mAb H-F-2A-L vector, significant anti-tumor activity was observed in the B16 melanoma model (P<0.05; FIG. 7). Administration of AAV8 CAG rat mAb H-F-2A-L vector in the B16F10 melanoma model also significantly prolonged the median survival time of mice (P<0.01; FIG. 8). Furthermore, in mice injected with AAV8 CAG rat mAb H-F-2A-L vector, significant anti-tumor activity was observed in the U87 glioma model (P<0.05; FIG. 9). Administration of AAV8 CAG rat mAb H-F-2A-L vector in the U87 glioma model also significantly prolonged the median survival time of mice (P<0.01; FIG. 10).

These results demonstrate that biologically active full-length monoclonal antibodies can be delivered by a single AAV vector administration in vivo resulting in long term expression of therapeutic antibody levels in the serum of mice.

Example 6

Preparation of AAV Vectors and Expression of a Human IgG From AAV H-F-2A-L Viruses In Vitro In another example of the invention, a full-length human anti-KDR mAb was expressed from an AAV vector similar to those described above for a rat monoclonal antibody. The AAV-8 vector includes a single promoter (CAG) driving a single open reading frame consisting of a sequence encoding the antibody heavy chain, a furin cleavage site, a 2A sequence, and a sequence encoding the antibody light chain for a full-length human anti-KDR mAb. An AAV plasmid encoding a human anti-KDR mAb driven by the CAG promoter and further includes a self processing cleavage sequence (2A) and an additional proteolytic cleavage site (e.g. Furin) was constructed as described in Example 1. To produce AAV vector, the AAV plasmid was purified using a plasmid DNA mega purification kit (Qiagen). The 293 cells were co-transfected with the AAV vector plasmids, a Rep/Cap plasmid for AAV8, and an adenovirus helper plasmid. After transfection, AAV viruses were purified from cell lysates by double CsCl gradient centrifugations, followed by extensive dialysis against PBS. The physical titers of rAAV virus were determined by dot blots with the probes using AAV plasmids as templates.

Figure 11:
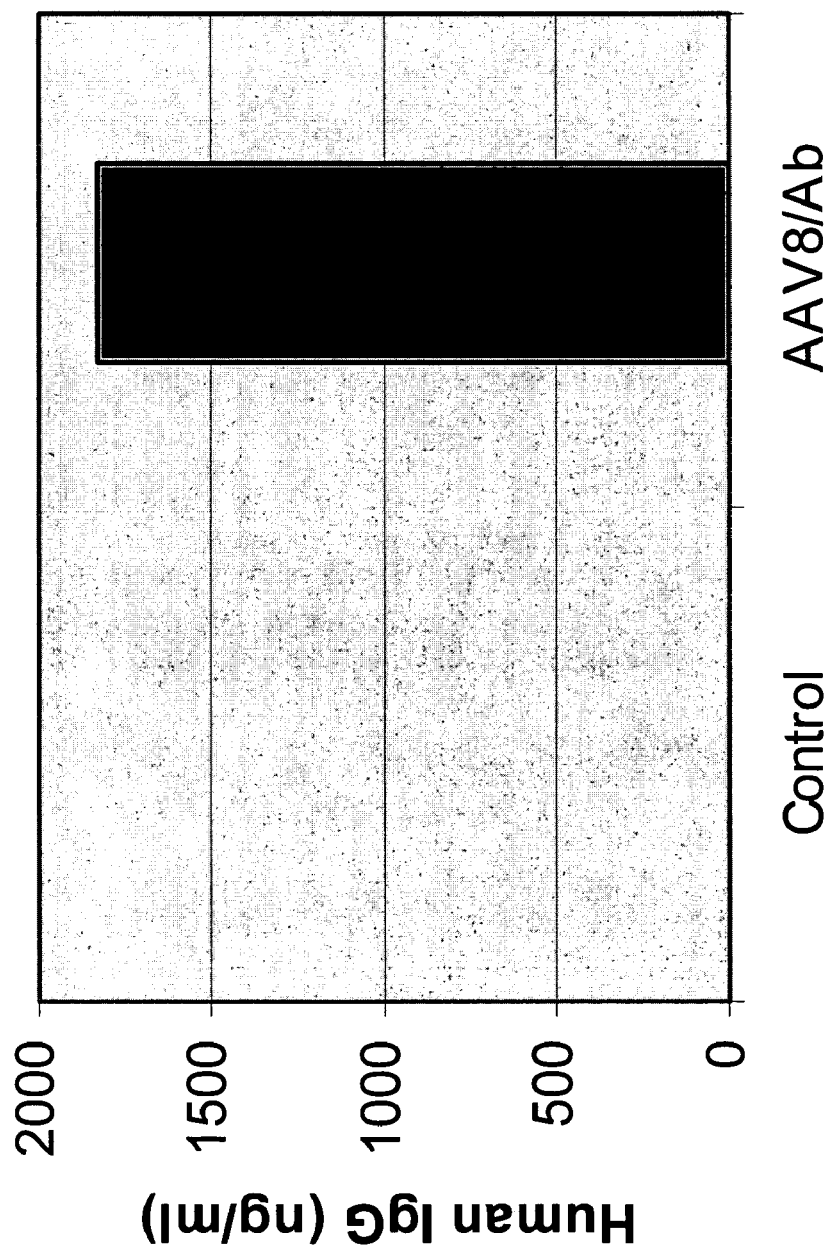
FIG. 11 shows the expression levels of a full length human anti-KDR antibody in cell culture supernatants of U87 cells transduced with an AAV8 vector encoding for the human anti-KDR monoclonal antibody heavy chain, a Furin cleavage sequence, a 2A sequence, and the antibody light chain (HF2AL), as described in Example 6.

To express the human anti-KDR mAb using the AAV viral vector in vitro, HuH7 glioma cells were cultured in 6-well plates and infected with the AAV vector by adding purified AAV8 CAG human mAb H-F-2A-L vector to the cells. After 72 hours, the cell culture supernatants were collected for analysis of human IgG1 expression using a human IgG1 kit (Zymed laboratories ). Human monoclonal antibody to KDR was detected in cell culture supernatants infected with $1 \times 10^5$ vp of AAV8 CAG H-F-2A-L vector but not in the supernatants infected with control vector not expressing any transgene (FIG. 11).

Example 7

Expression of Two Human IgG Subclasses From AAV H-F-2A-L Viruses In Vivo

Figure 12:
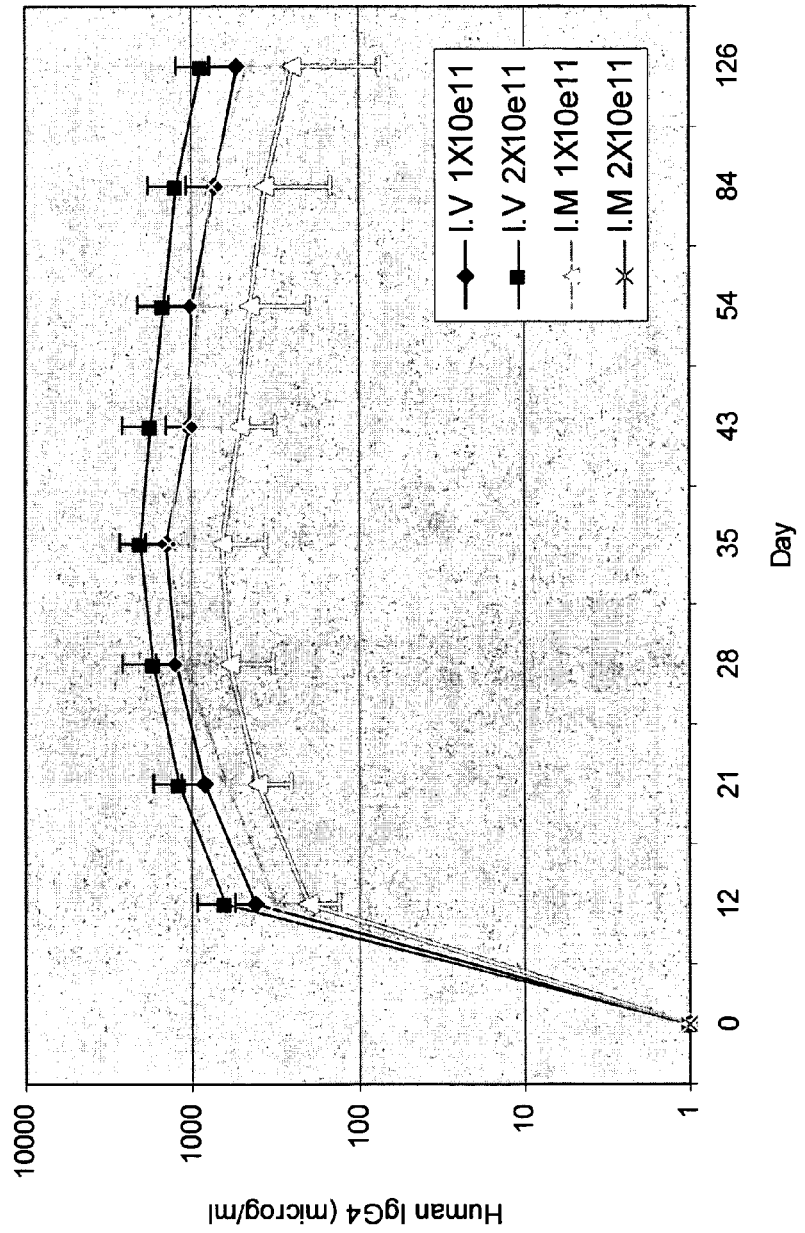
FIG. 12 depicts the in vivo antibody (IgG$_4$) expression level (ug/ml) in mouse serum following intravenous (i.v.) injection or intramuscular (i.m.) injection of $1 \times 10^{11}$ vp or $2 \times 10^{11}$ vp of an AAV 8 vector encoding the antibody heavy chain, a furin cleavage site, a 2A sequence, and the antibody light chain (HF2AL) for a human anti-KDR antibody, where the antibody is expressed under the control of a hybrid promoter/enhancer that consists of the cytomegalovirus promoter and enhancer sequences, chicken beta-actin (CAG) promoter and enhancer sequences and a chimeric intron.

The AAV vector encoding the full-length human anti-KDR mAb described in Example 2 and shown to produce biologically active, full-length IgG4 antibody in vitro in Example 6 was used to express full-length IgG4 antibody in vivo in nude mice. AAV8 CAG H-F-2A-L or AAV control vector ($1 \times 10^{11}$ or $2 \times 10^{11}$ virus particles/mouse) was administered intravenously (i.v.) or intramuscularly (i.m.) into nude mice. Mice were bled at the indicated intervals and the serum levels of the human anti-KDR mAb were determined by ELISA, essentially as described for rat antibody levels in Example 5, except an anti-human IgG4 antibody and human IgG4 protein standard were used. Mice injected with $2 \times 10^{11}$ vp per mouse via either route of administration showed high serum mAb (IgG4) concentrations of more than 1 mg/ml and sustained levels of human antibody of 881 ug/ml for intravenous injection or 459 ug/ml for intramuscular injection were observed at 18 weeks (FIG. 12). No human mAb was detected in the serum of control mice (data not shown).

For the expression of IgG1 subclass, the nucleotide sequences encoding the constant region of the heavy chain of the human anti-KDR antibody of the AAV 8 CAG H-F-2A-L vector described above were replaced with the corresponding nucleotide sequences encoding constant region of heavy chain of human IgG1 subclass. The IgG1-encoding AAV 8 vector was prepared and purified essentially as described in Example 6 and $2 \times 10^{11}$ vp per mouse were administered intravenously (i.v.) in to nude mice. Mice were bled at days 10, 21 and 35 and human IgG1 mAb serum levels were determined by ELISA, essentially as described above, except using an anti-human IgG1 antibody and human IgG1 protein standard. Increasing concentrations of human anti-KDR (IgG1) mAb were observed in serum with levels of human antibody of about 100 micrg/ml at Day 35.

The results of these experiments demonstrate that full-length, human antibodies of varying IgG subclass may be expressed at high levels in vivo from a single administration of the AAV vectors of the present invention.

Example 8

Human Anti-KDR MAB Stimulates Human Endothelial Cell Proliferation In Vitro

XENOMOUSE™ transgenic mice that express human IgG were immunized with recombinant KDR to generate human anti-KDR antibody. The lymphocytes from the immunized mice were harvested to generate hybridoma cells. Antibody clones were screened based on their binding to KDR in an ELISA-based assay. One of the clones, CG2.20, exhibited high affinity to KDR and showed an agonistic effect on endothelial cell assays (as further described below). This antibody was characterized as IgG4 kappa and fully human.

Figure 13:
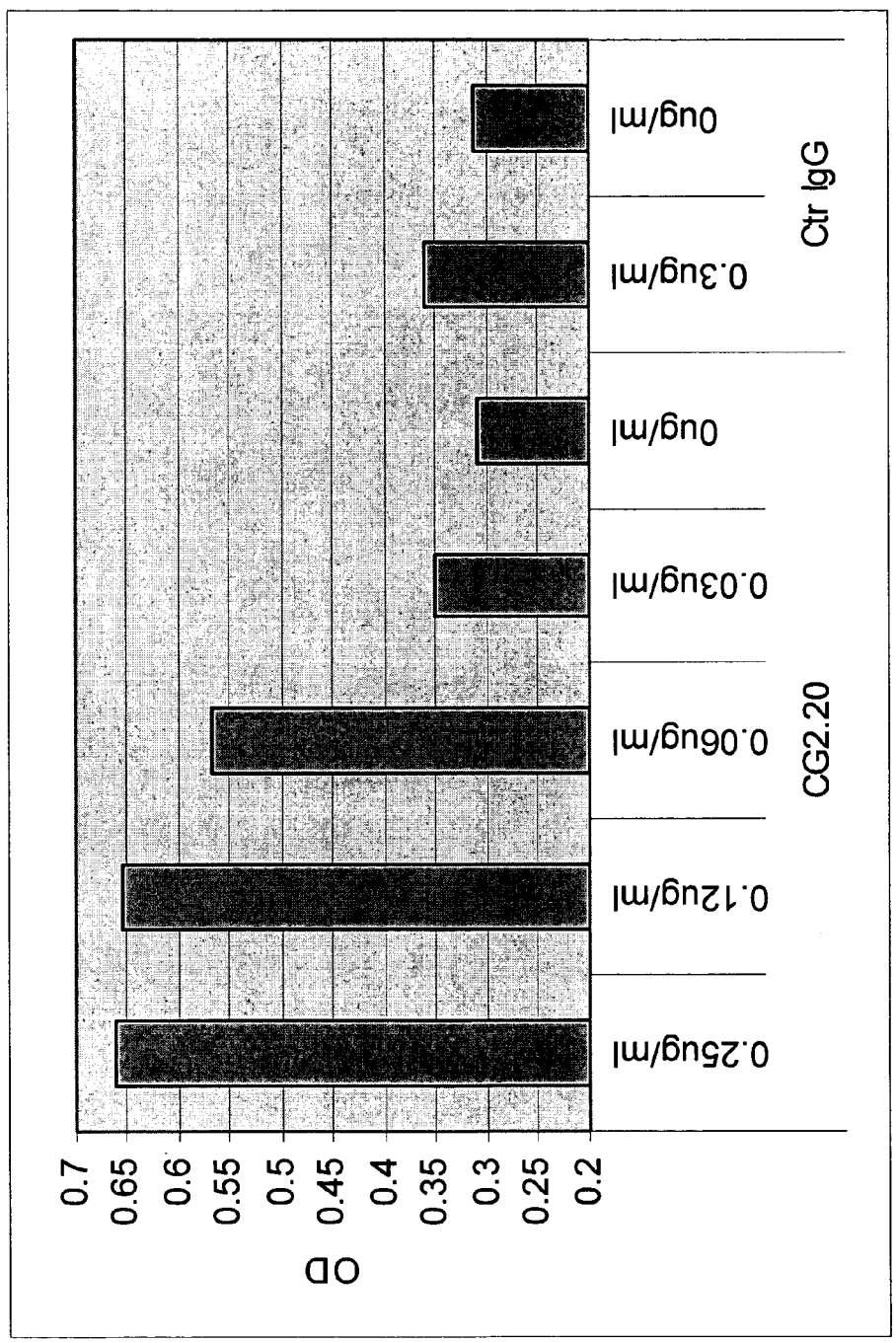
FIG. 13 shows the dose-response effect of an exemplary agonistic anti-KDR monoclonal antibody, CG2.20 on HUVEC cell proliferation in vitro.

The biological activity of the anti-KDR antibody (CG2.20) was determined in a human endothelial cell proliferation assay. In this assay, HUVEC cells (Clonetics) were seeded in 96 well plates at 5000 cells/well and cultured in EGM complete medium overnight. The following day, each well was rinsed with PBS and fed with 200 ul of EBM basal medium containing 1% fetal bovine serum and various amounts of purified anti-KDR antibody (CG2.20) or control IgG. No VEGF or other growth factors were included in the medium. After 3 days, a CCK8 reagent (CCK8 kit, Dojindo Laboratories) was added and relative cell densities were determined based on OD readings at 450 nm. As shown in FIG. 13, addition of CG2.20 antibody increased cell proliferation of HUVEC cells in a dose-dependent manner.

TABLE 4

Brief Table Of The Sequences

| SEQ ID | SEQUENCE | DESCRIPTION |
|---|---|---|
| 1 | LLNFDLLKLAGDVESNPGP | FMDV 1A amino acid sequence |
| 2 | TLNFDLLKLAGDVESNPGP | FMDV 2A amino acid sequence |
| 3 | LLKLAGDVESNPGP | Exemplary self processing amino acid sequence |
| 4 | NFDLLKLAGDVESNPGP | Exemplary self processing amino acid sequence |
| 5 | QLLNFDLLKLAGDVESNPGP | Exemplary self processing amino acid sequence |
| 6 | APVKQTLNFDLLKLAGDVESNPGP | Exemplary self processing amino acid sequence |
| 7 | VTELLYRMKRAETYCPRPLLAIHPTEARH KQKIVAPVKQTLNFDLLKLAGDVESNPGP | Exemplary self processing amino acid sequence |
| 8 | LLAIHPTEARHKQKIVAPVKQTLNFDLLK LAGCVESNPGP | Exemplary self processing amino acid sequence |
| 9 | EARHKQKIVAPVKQTLNFDLLKLAGDVE SNPGP | Exemplary self processing amino acid sequence |
| 10 | Furin cleavage site with the consensus sequence RKR(R)R | Exemplary additional proteolytic cleavage site |
| 11 | Furin cleavage site RAKR | Exemplary additional proteolytic cleavage site |
| 12 | Factor Xa cleavage site: IE(D)GR | Exemplary additional proteolytic cleavage site |
| 13 | Signal peptidase I cleavage site: e.g. LAGFATVAQA | Exemplary additional proteolytic cleavage site |
| 14 | Thrombin cleavage site: LVPRGS | Exemplary additional proteolytic cleavage site |

What is claimed is:

1. An adeno-associated virus (AAV) vector for expression of a recombinant immunoglobulin or a fragment thereof, comprising:
in the 5' to 3' direction, a promoter operably linked to all of (1) a coding sequence for the heavy chain of the immunoglobulin or the fragment thereof, (2) a coding sequence for a furin cleavage site, wherein the coding sequence for the furin cleavage site encodes an oligopeptide selected from the group consisting of SEQ ID NO:15, SEQ ID NO:16, SEQ ID NO:17, and SEQ ID NO:18, and wherein each of the amino acids encoded in the coding sequence for the furin cleavage site is cleavable by a carboxypeptidase, (3) a coding sequence for a 2A self-processing cleavage site and (4) a coding sequence for the light chain of an immunoglobulin or the fragment thereof, wherein the recombinant immunoglobulin or the fragment thereof binds an antigen.

2. The vector according to claim 1, wherein said coding sequence for the 2A self-processing cleavage site is a Foot and Mouth Disease Virus (FMDV) sequence.

3. The vector according to claim 2, wherein the coding sequence for the 2A self-processing cleavage site encodes an oligopeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9.

4. The vector according to claim 1, wherein the promoter is selected from the group consisting of an elongation factor 1-alpha promoter (EF 1-alpha) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter.

5. The vector according to claim 4, wherein said promoter is a CAG hybrid promoter/enhancer.

6. The vector according to claim 4, wherein said promoter is an elongation factor 1-alpha promoter (EF1a) promoter.

7. The vector according to claim 1, wherein said coding sequence for the heavy chain of the immunoglobulin or the fragment thereof and the coding sequence for the light chain of the immunoglobulin or the fragment thereof are expressed in an equimolar ratio or close to equimolar ratio.

8. The vector according to claim 1, wherein said AAV vector is an AAV6 vector.

9. The vector according to claim 1, wherein said AAV vector is an AAV8 vector.

10. An isolated host cell transduced with the vector of claim 5.

11. An isolated host cell transduced with the vector of claim 1.

12. A method for producing a recombinant immunoglobulin or a fragment thereof, comprising:
a. transducing a host cell with the vector according to claim 1; and
b. expressing said recombinant immunoglobulin or the fragment thereof in said transduced host cell, wherein said coding sequence for the heavy chain of the immunoglobulin or the fragment thereof and said coding sequence for the light chain of the immunoglobulin or the fragment thereof are expressed in a substantially equimolar ratio, wherein the recombinant immunoglobulin or the fragment thereof contains no amino acids from said furin cleavage site.

13. The method according to claim 12, wherein said coding sequence for the 2A self-processing cleavage site is a Foot and Mouth Disease Virus (FMDV) sequence.

14. The method according to claim 13, wherein the coding sequence for the 2A self-processing cleavage site encodes an oligopeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9.

15. A method for expressing a recombinant immunoglobulin or a fragment thereof in vivo comprising
a) administering the vector according to claim 1 to a mammal, wherein said vector is administered by a route selected from the group consisting of portal vein injection, intramuscular injection, intratumoral injection and intraperitoneal injection; and
b) expressing the recombinant immunoglobulin or the fragment thereof wherein said coding sequence for the heavy chain of the immunoglobulin or the fragment thereof and said coding sequence for the light chain of the immunoglobulin or the fragment thereof are expressed in a substantially equimolar ratio, wherein the recombinant immunoglobulin or the fragment thereof contains no amino acids from said furin cleavage site.

16. The method according to claim 15, wherein said recombinant immunoglobulin or fragment thereof is a full length recombinant immunoglobulin that is expressed in vivo for at least 3 months.

17. The method according to claim 15, wherein said recombinant immunoglobulin or fragment thereof is a full length recombinant immunoglobulin that is expressed at a level of at least 1 mg/ml.

* * * * *